(12) United States Patent
Moon et al.

(10) Patent No.: US 10,568,902 B2
(45) Date of Patent: Feb. 25, 2020

(54) MODULATED GUANIDINE-CONTAINING POLYMERS OR NANOPARTICLES

(71) Applicants: Joong Ho Moon, Weston, FL (US); Md Salauddin Ahmed, Comilla (BD)

(72) Inventors: Joong Ho Moon, Weston, FL (US); Md Salauddin Ahmed, Comilla (BD)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 16/220,801

(22) Filed: Dec. 14, 2018

(65) Prior Publication Data

US 2019/0183923 A1 Jun. 20, 2019

Related U.S. Application Data

(60) Provisional application No. 62/598,578, filed on Dec. 14, 2017.

(51) Int. Cl.
| | |
|---|---|
| A61K 31/785 | (2006.01) |
| A61K 47/54 | (2017.01) |
| A61P 35/00 | (2006.01) |
| B82Y 5/00 | (2011.01) |

(52) U.S. Cl.
CPC .......... *A61K 31/785* (2013.01); *A61K 47/545* (2017.08); *A61P 35/00* (2018.01); *B82Y 5/00* (2013.01)

(58) Field of Classification Search
CPC .................................................. A61K 31/785
See application file for complete search history.

(56) References Cited

U.S. PATENT DOCUMENTS

| | | | |
|---|---|---|---|
| 9,676,886 B2 | 6/2017 | Moon et al. | |
| 9,757,410 B2 | 9/2017 | Moon et al. | |
| 2015/0307526 A1* | 10/2015 | Griesgraber | C07F 7/1872 435/183 |

OTHER PUBLICATIONS

Manetti et al., J Med Chem, 2009, 32, 7376-7379.*
Ahmed, M.S. et al. "Synthesis of Antimicrobial Poly(guanylurea)s," *Bioconjugate Chem.*, 2018, pp. 1006-1009, vol. 29.
Chinnapaiyan, S. et al. "Cigarette smoke promotes HIV infection of primary bronchial epithelium and additively suppresses CFTR function," *Sci. Rep.*, 2018, pp. 7984-7993, vol. 8, No. 1.
Kapp, T.G. etal. "Small Cause, Great Impact: Modification of the Guanidine Group in the RDG Motif Controls Integrin Subtype Selectivity," *Angew. Chem. Int. Ed.*, 2016, pp. 1540-1543, vol. 55.
Miyabe, H. et al. "Palladium- or Iridium-Catalyzed Allylic Substitution of Guanidines: Convenient and Direct Modification of Guanidines," *J. Org. Chem.*, 2009, pp. 305-311, vol. 74.
Unwalla, H.J. et al. "Albuterol Modulates Its Own Transepithelial Flux via Changes in Paracellular Permeability," *Am J Respir Cell Mol Biol*, 2012, pp. 551-558, vol. 46, No. 4.
Unwalla, H.J. et al. "Transforming Growth Factor-β1 and Cigarette Smoke Inhibit the Ability of β$_2$-Agonists to Enhance Epithelial Permeability," *Am J Respir Cell Mol Biol*, 2015, pp. 65-74, vol. 52, No. 1.

* cited by examiner

*Primary Examiner* — Kyle A Purdy
(74) *Attorney, Agent, or Firm* — Saliwanchik, Lloyd & Eisenschenk

(57) ABSTRACT

A modulated guanidine substituted polymer or nanoparticle has a guanidine moiety or on a plurality of repeating units of a polymer or on the surface of a nanoparticle where the guanidine moiety is modulated as a substituted amidinourea or amidinocarbamate or salt thereof. The modulated guanidine substituted polymer or nanoparticle can be prepared by direct amination of a N-Boc protected guanidine substituted conjugated polymer or N-Boc protected guanidine substituted nanoparticle, where an amine or alcohol is combined in solution or suspension with the protected conjugated polymer or nanoparticle and the resulting mixture is heated. The modulated guanidine substituted polymer or nanoparticle can be used in a cancer treatment formulation.

17 Claims, 17 Drawing Sheets

*compared with siRNA alone

MODULATED GUANIDINE-CONTAINING POLYMERS OR NANOPARTICLES

CROSS-REFERENCE TO A RELATED APPLICATION

This application claims the benefit of U.S. Provisional Application Serial No. 62/598,578, filed Dec. 14, 2017, the disclosure of which is hereby incorporated by reference in its entirety, including all figures, tables and drawings.

This invention was made with government support under DMR1352317 awarded by the National Science Foundation. The government has certain rights in the invention.

BACKGROUND OF INVENTION

Ovarian cancer (OVCA) is the most lethal gynecologic malignancy. The majority of patients are diagnosed with advanced disease, which ultimately recurs, and they die from the disease. OVCA is becoming resistant to current chemotherapies, including the two most commonly used first-line drugs taxol and cisplatin, and patients are exhausting their treatment options. Multidrug resistance (MDR) is closely related to overexpression of membrane efflux proteins (e.g., P-glycoprotein) and anti-apoptotic proteins [e.g., survivin and myeloid cell leukemia 1 (Mcl-1)]. Because small RNA molecules, including small interfering RNA (siRNA), have an extraordinary ability to knock down gene expression, RNA interference (RNAi) induced by small RNA molecules can be an excellent solution for overcoming MDR. RNA molecules are highly susceptible for enzymatic degradation and too big to penetrate the cellular membranes. Although various types of delivery materials have been developed and used at the in vitro tissue culture level, gene regulation at the ex vivo or in vivo level has been largely unsuccessful due to poor intracellular siRNA availability. Lack of targeting and inefficient intracellular entry of drugs requires over dosing, which is also responsible for poor therapeutic outcomes. Efficient delivery of negatively charged RNA molecules to target cells is pivotal for a successful application of RNAi technology. Innovative therapeutic delivery techniques are urgently needed to address the drug resistance and poor intracellular entry efficiency.

In human airway epithelium possessing additional extracellular barriers, such as mucus layers, transfection using conventional lipid-based or positively charged carriers is extremely limited. As the critical physical barrier interfacing environmental stimuli, the mucosal surfaces of epithelium tightly regulate various physiological and immunological processes. In the mucus layer, dense mucin fibers and negatively charged proteoglycans provide the adhesive and viscous protective layer that often trap and remove positively charged carriers, resulting in poor delivery of payloads to the underlying epithelial cells. Very few options are currently available for delivering nucleic acids to the airway epithelium. Mucus-altering or mucolytic agents can be used as adjuvants of gene carriers, although high millimolar concentrations are often needed to disrupt or disturb the mucus layers.

Alternatively, block copolymers of polyethyleneimine (PEI) and polyethyleneglycol (PEG) have been developed to deliver plasmid DNA (pDNA) to the lung airways. Positively charged PEI and negatively charged pDNA form ionic complexes, while the PEG block shields the positively charged block from the negatively charged mucus layers and provides diffusion through nanometer sized mucus meshes. However, the PEG block often causes poor gene complexation and reduced cellular entry; and pDNA can form smaller ionic complexes with PEI-PEG copolymers due to the molecular topography of pDNA, enabling compaction to nanoparticles. Although optimization provides the opportunity to balance the ratios between charged and PEG segments, block copolymer architectures in biological fluids containing ions and proteins complicate surface properties and influence biological functions.

Short peptides or their synthetic mimics of the protein's translocation domains are excellent materials to introduce therapeutic agents to intracellular compartments rapidly. The fast entry of those materials is associated with a combination of membrane pore formation and non-receptor-mediated endocytosis. Combinations of ionic bonding, hydrogen bonding, and hydrophobic interactions influence the entry pathways. However, coupling cell penetrating peptides to therapeutic proteins or nucleic acids often alters the entry pathways, resulting in decreased intracellular availability. Fluorescent labels needed to study the entry mechanism and the localization of synthetic materials influences the materials physical properties and cellular behaviors toward the materials. The development of nontoxic biomaterials exhibiting superior cellular entry and therapeutic delivery is needed to substantially increase therapeutic efficacy of these systems.

In another approach, nanometer sized particles accumulate in relatively loosely organized tumor tissues as opposed to tight normal tissue. When the particulates are modified with ligands specific to the receptors overexpressed on cancer cell surfaces, targeting at the tissue level can be further improved. Unfortunately, overall therapeutic efficacy remains unsatisfactory due to poor intracellular entry and a lack of organelle targeting. Endocytosis mediated by cell surface receptors is the primary entry pathway, but it is often slow and inefficient. Endocytosed therapeutic agents undergo degradation in endosomes and lysosomes or in recycling processes, such as exocytosis, which lower the intracellular concentration of therapeutic agents. By not involving in endosome escaping process, direct membrane translocation offers high intracellular concentrations of therapeutics. Nanometer sized particles with modulated surface properties is pivotal for efficient intracellular delivery and labeling because the surface properties are closely related to their initial interaction following entry.

Aromatic π-electron conjugated polymers (CPs) are innovative fluorescent materials that have a high potential as therapeutic carriers. Because of excellent photophysical properties, such as high brightness and sensing ability, and excellent biophysical properties, such as biocompatibility, nontoxicity, high cellular interaction, and ease of entry, CPs have been used for live cell and tissue imaging, biochemical sensing, and gene and drug delivery. In addition to intrinsic fluorescent properties that are highly advantageous for labeling and tracking, the charged CPs are structurally similar in charge density and backbone rigidity to materials known for exhibiting efficient cellular entry, such as tyrosine aminotransferase (TAT) as shown in FIG. 1. Because of a rigid hydrophobic backbone and a flexible hydrophilic charged side chains, CPs can bind to and enter through cellular membranes.

Moon et al. U.S. Pat. Nos. 9,676,886 and 9,757,410 discloses biodegradable CPs by introducing flexible degradable functional groups along the backbone of the CP that can be used for quantitative labeling of mitochondria. Cellular interaction and internalization of CPs are dependent on the chemical structures of both the backbone and side chains of the CPs. CPs with guanidine units (G-CPs) having molecular weights of ~14,000 g/mol enter live cells quickly, within 10 minutes upon incubation, through the cancer cell membrane.

Conventional method of synthesizing CPs with diverse functional group is tedious and problematic. In addition to intrinsic synthetic challenge of optimizing polymerization conditions for each monomer, the resulting CP with different functional group will have different molecular weight and polydispersity, which will influence their physical and biophysical behaviors. It is therefore desirable to form a nanoparticle or a CP that has attached modified guanidine moieties. These may provide rapid and tailored cellular delivery of anti-MDR siRNA for dramatically enhanced chemotherapy efficiencies that can dramatically impact cancer treatment.

DETAILED DISCLOSURE

Figure 1:
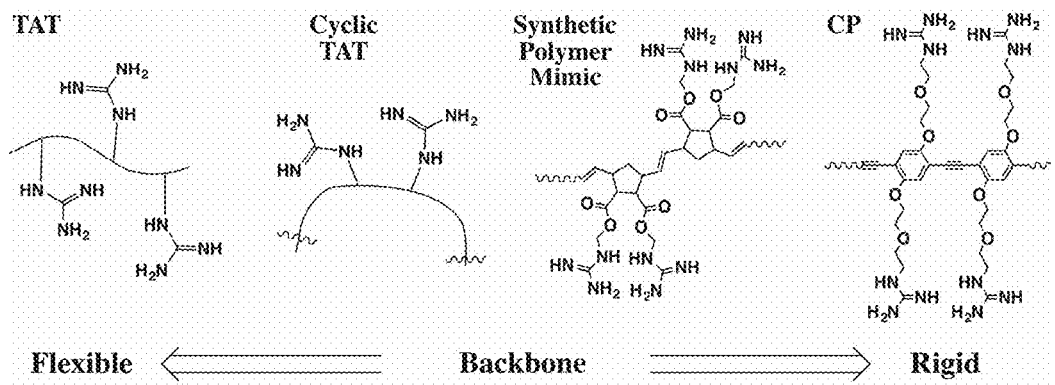
FIG. 1 shows a schematic comparison of flexible tyrosine aminotransferase (TAT) synthetic mimics vs the backbone rigidity of the guanidine comprising conjugated polymer, (G-CP).
Figures 2A, 2B:
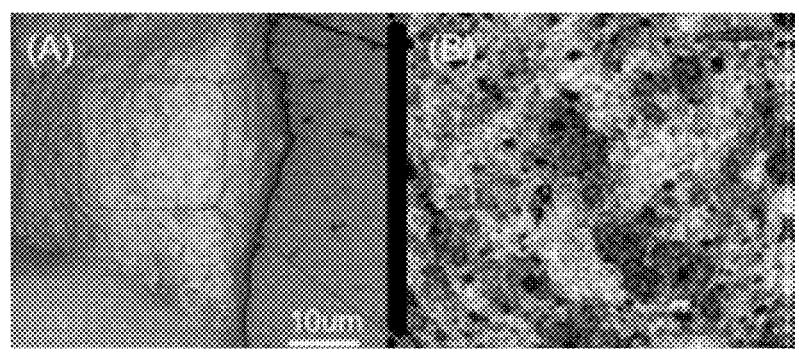
FIG. 2A shows a scanning ion-conductance microscopy (SICM) image of HeLa cells treated with G-CP.
FIG. 2B shows a magnified image where the pore formation on the surface of the HeLa cells has been induced by the G-CP.
Figure 2C:
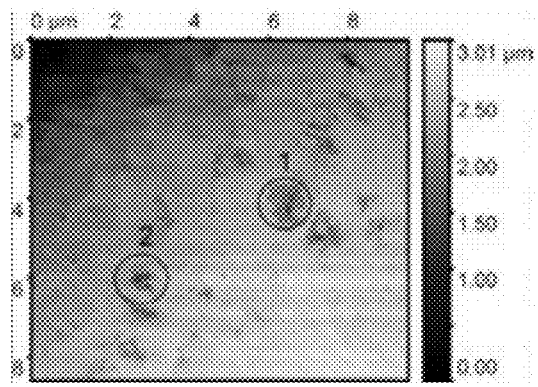
FIG. 2C shows a SICM topographic image of the HeLa cells treated with G-CP and labeled with m-Cherry protein.
Figure 2D:
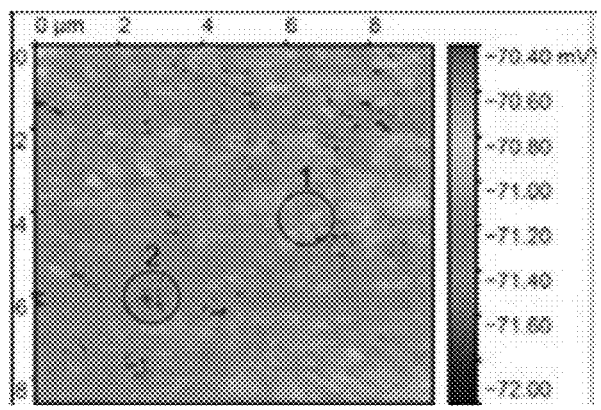
FIG. 2D shows a SICM potential map of the same area as FIG. 2C showing the presence of numerous pores.
Figure 2E:
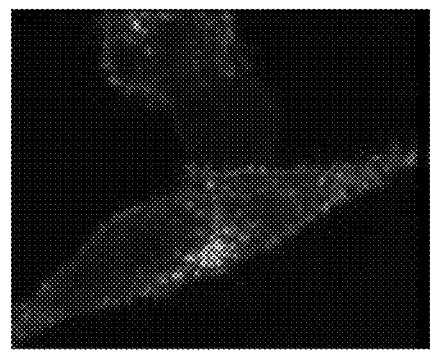
FIG. 2E shows a confocal microscopic image of HeLa cells incubated with fluorescing G-CP for 10 min supporting fast cellular entry of G-CP.

Biodegradable CPs can be formed by introducing flexible degradable functional groups along the backbone of the CP that can be used for quantitative labeling of mitochondria. Cellular interaction and internalization of CPs are dependent on the chemical structures of both the backbone and side chains of the CPs. CPs with guanidine units (G-CPs), as disclosed in Moon et al. U.S. Pat. Nos. 9,676,886 and 9,757,410, and incorporated herein by reference, that have molecular weights of ~14,000 g/mol, enter live cells quickly through the cancer cell membrane. After generating positive charges on guanidine, the resulting polymers are soluble in DMSO, and form nanoparticles in PBS buffer with a hydrodynamic diameter of about 56 nm. Live cells treated with CPs containing various functional groups display surface morphologies at the submicron level that are dependent on the chemical functionalities of the CPs. As can be seen in FIGS. 2A and 2B, the scanning ion conductance microscopy images indicate pores on the cells surface. The potential at pores are lower than for the rest of the area, suggesting formation of pore-like features on the membrane (FIGS. 2C and 2D). Based on the difference potentials at the topographic pores, different stages of cellular entry of CP are suggested (FIG. 2E). Confocal microscopic imaging also supports fast and efficient cellular entry of G-CP. Within 10 min, a significant amount of G-CP was found in the intracellular compartments.

Ideal small interfering RNA (siRNA) delivery requires RNA protection, excellent pharmacokinetics, targeting, cellular entry, and release of siRNA in the cytosol of target cells. The biophysical properties of positively charged carriers complexed with negatively charged siRNA can he tailored by introducing functional groups at the positive charge. Positively charged carriers often exhibit toxic effects and promote high blood clearance through opsonization, limiting clinical applications.

Figure 3:
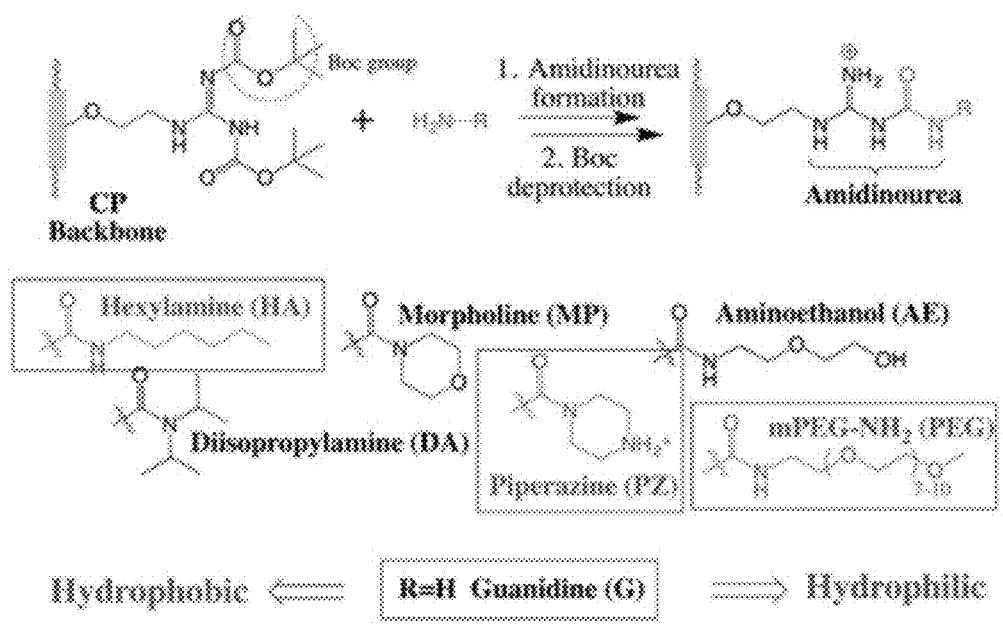
FIG. 3 shows a scheme for the modulation of the chemical environment at the guanidine group by amidinourea formation, according to an embodiment of the invention.
Figure 4A:
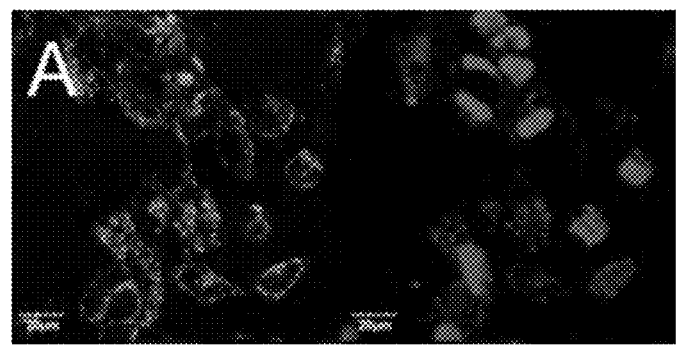
FIG. 4A show a fluorescent microscopic images of HeLa cells incubated with modulated guanidine complex for 1 h where the modulating amine was aminoethoxyethanol to form a hydrophilic G-CP, Poly-2, according to an embodiment of the invention, with CP shown in the left panel and siGLO on the right panel.
Figure 4B:
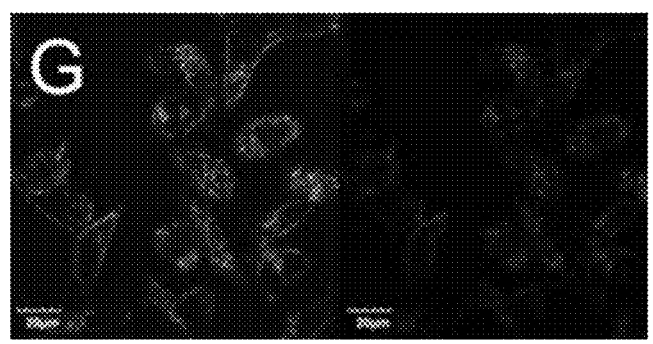
FIG. 4B show a fluorescent microscopic images of HeLa cells incubated with guanidine complex for 1 h to form a G-CP, Poly-2, with CP shown in the left panel and siGLO on the right panel.
Figure 4C:
FIG. 4C show a fluorescent microscopic images of HeLa cells incubated with modulated guanidine complex for 1 h where the modulating amine was morpholine to form a slightly hydrophobic G-CP, according to an embodiment of the invention, with CP shown in the left panel and siGLO on the right panel.
Figure 4D:
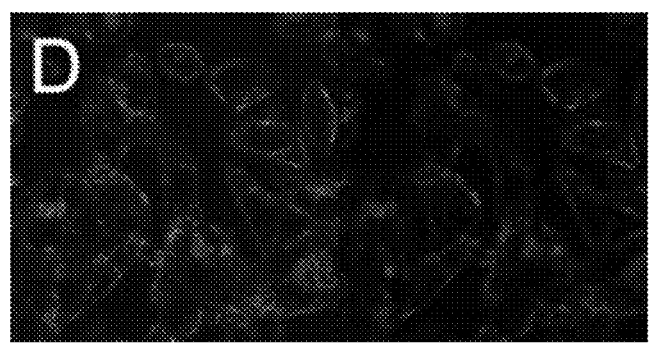
FIG. 4D show a fluorescent microscopic images of HeLa cells incubated with modulated guanidine complex for 1 h where the modulating amine was diisopropylamine to form a hydrophobic G-CP, according to an embodiment of the invention, with CP shown in the left panel and siGLO on the right panel.

According to an embodiment of the invention, on-ionic group, including, but not limited to, hydrophobic lipids and hydrophilic PEGs, at the positive charge improve carriers' biophysical properties, provided that the modification does not diminish the ionic complexation and cellular entry. Unlike modulated guanidine on TAT peptides, which decreases entry efficiency, G-CPs modulated with various functional groups exhibit enhance biophysical properties. Modulated G-CPs, according to an embodiment of the invention, as shown in FIG. 3, have an aminoethoxyethanol groups at the positive charge of the guanidines to increase the efficiency of cellular entry and siRNA delivery, as illustrated in FIG. 4A vs FIG. 4B for guanidines, while exhibiting no viability inhibition. Addition of a morpholine group at the charged guanidine changed the cellular entry behaviors dramatically, as shown in FIG. 4C, as indicated by the diffused uniform staining of the cytosol. Addition of a bulky diisopropylamine group at the charged guanidine appears to diminish the cellular entry behavior, as shown in FIG. 4D. Modulating the charged group with specialized functional groups, such as, but not limited to, tumor cell surface targeting ligands, PEG, or drugs, can offer tailored cellular targeting and entry to achieve optimized therapeutic efficacy. Because the drug and gene knockdown efficacy is highly unique on each tumor due to the unique tumor microenvironment, no generalized carrier will work equally on each tumor. Modulation, as indicated above, allows facile optimization for a tumor because of the straightforward chemical modulation chemistry that can be carried out. Any commercially available amine or alcohol, which can be readily transformed to an amine, or alcohol can be directly coupled to guanidine via the Mitsnobu reaction, can be added to the positively charged guanidine group. Using this synthetic approach to modulated G-CPs, a library of potential agents for screening and ultimate use against specific tumor types can be tailored for cellular entry and efficacy. Because the conventional and frequently used tumor cell lines have significantly different cellular features from patient tumors, drug delivery systems developed and optimized using the conventional cell lines can have large discrepancies in therapeutic efficacy when drugs are administered to patients.

Modulating the chemical environments at the positively charged guanidine functional group of the CP is used to optimize siRNA delivery. Embodiments of the invention are directed to a method to form CPs where there is introduced various functional groups of hydrophilic or hydrophobic molecules at the guanidine group, as can be seen in FIG. 3 of such CPs. The modulated CPs exhibit enhanced cellular entry, modulated intracellular localization, and better siRNA delivery. The modulated CPs promote: enhanced siRNA delivery by G-CP modulated with functional groups including short ethylene glycol (EG); efficient knockdown of MDR associated genes; and increased drug potency over cancer cells. The fine-tuning allows better protection, cellular entry, and release of siRNA. Less siRNA can be used for controlling the gene expression levels. The conjugated polymers (CPs), according to embodiments of the invention, are macromolecules with highly delocalized π-conjugated backbones and amphiphilic side chains. Cps display large absorption extinction coefficients, amplified quenching, high quantum yields, and tunable absorption and emission maxima Guanidine is a part of the side chain of arginine and remains charged over a wide pH range, which is reflected in the high pKa value (12.48) of its protonated counterpart. There are a great number of guanidine moieties peptides available due to their ease of modification and straightforward synthetic strategy. Guanidinum groups provide the CPs with cationic properties and act as mimics of cell-penetrating peptides (CPPs), molecular recognition, and antimicrobial agent.

Chemical modulation at the positive charge of a guanidinium-containing modulated CP is shown to efficiently knockdown a target gene of a well-differentiated primary human bronchial epithelium cells, which closely mimic many in vivo phenotypes of airway epithelium including: regulation of ion transport; mucous secretion; and mucociliary clearance. Not to be bound by a mechanism, the positive charges needing for ionic complexation of siRNA appears to increase adsorption to a mucus layer, resulting in decreased transfection efficiency and higher blood clearance by absorbing various serum proteins. In embodiments of the invention, amidinourea formation introduces hydrophilic PEG-like functional groups at the positive charge by reacting Boc-protected guanylurea to address these shortcomings.

Figure 5:
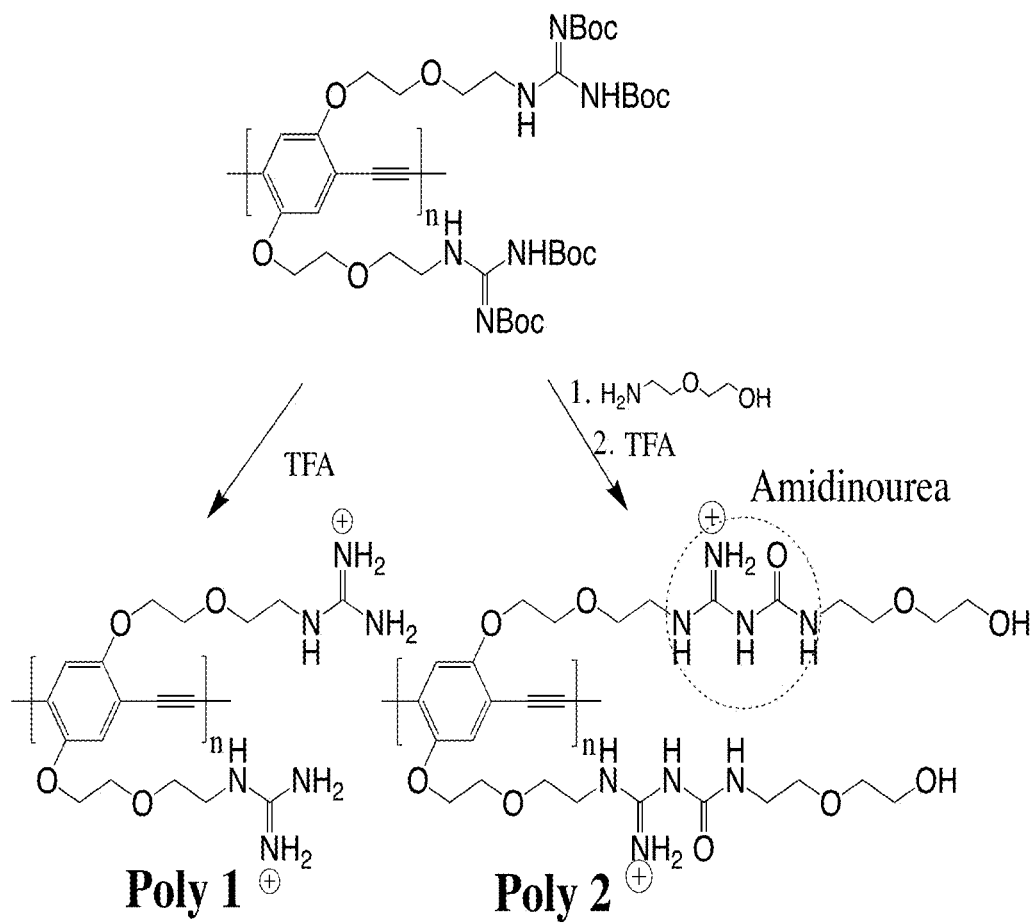
FIG. 5 is a reaction scheme for the preparation of Poly-1 and Poly-2 of a G-CP, according to an embodiment of the invention.
Figure 6A:
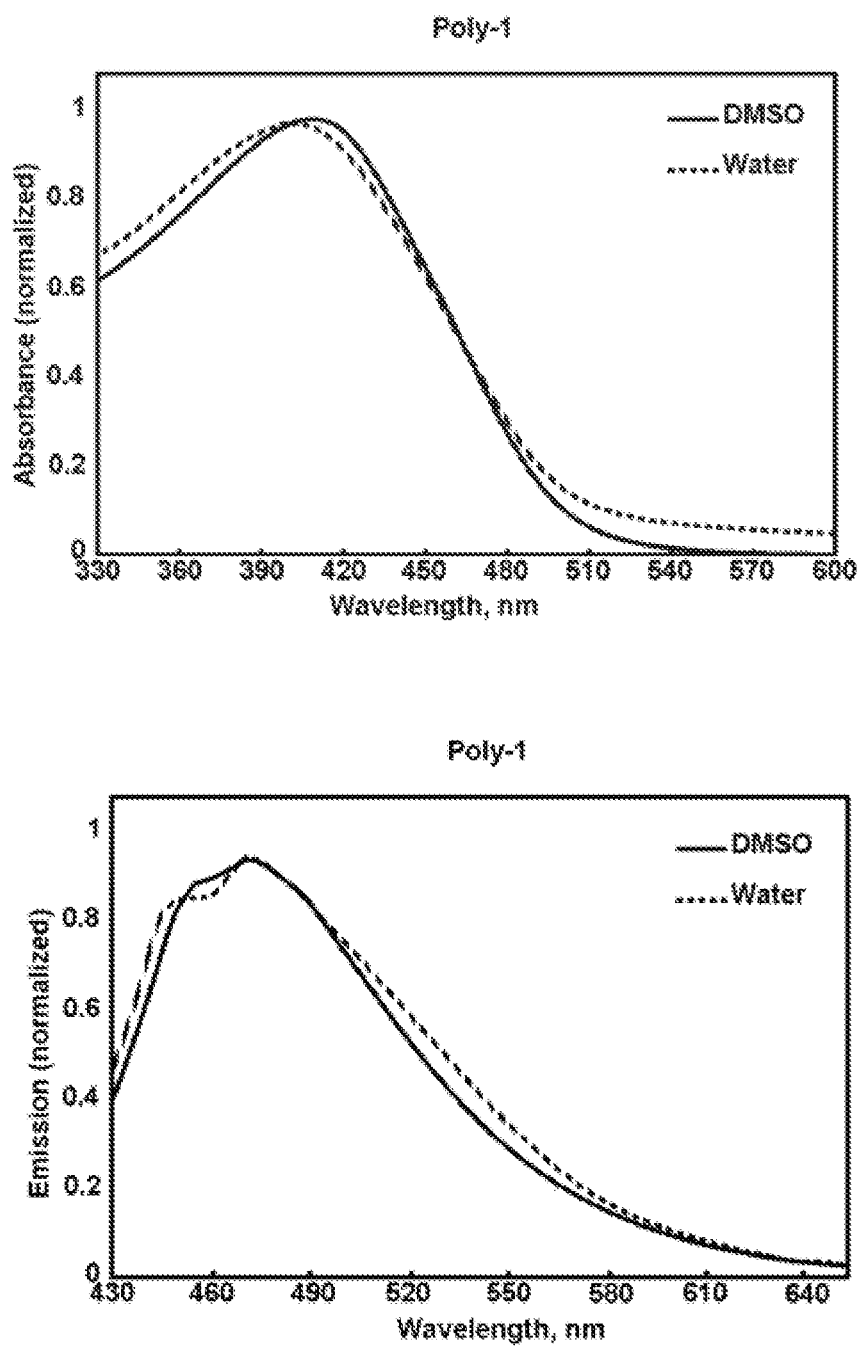
FIG. 6A shows UV absorbance (left) and emission (right) spectra of Poly-1 in DMSO and 95% water/5%DMSO.
Figure 6B:
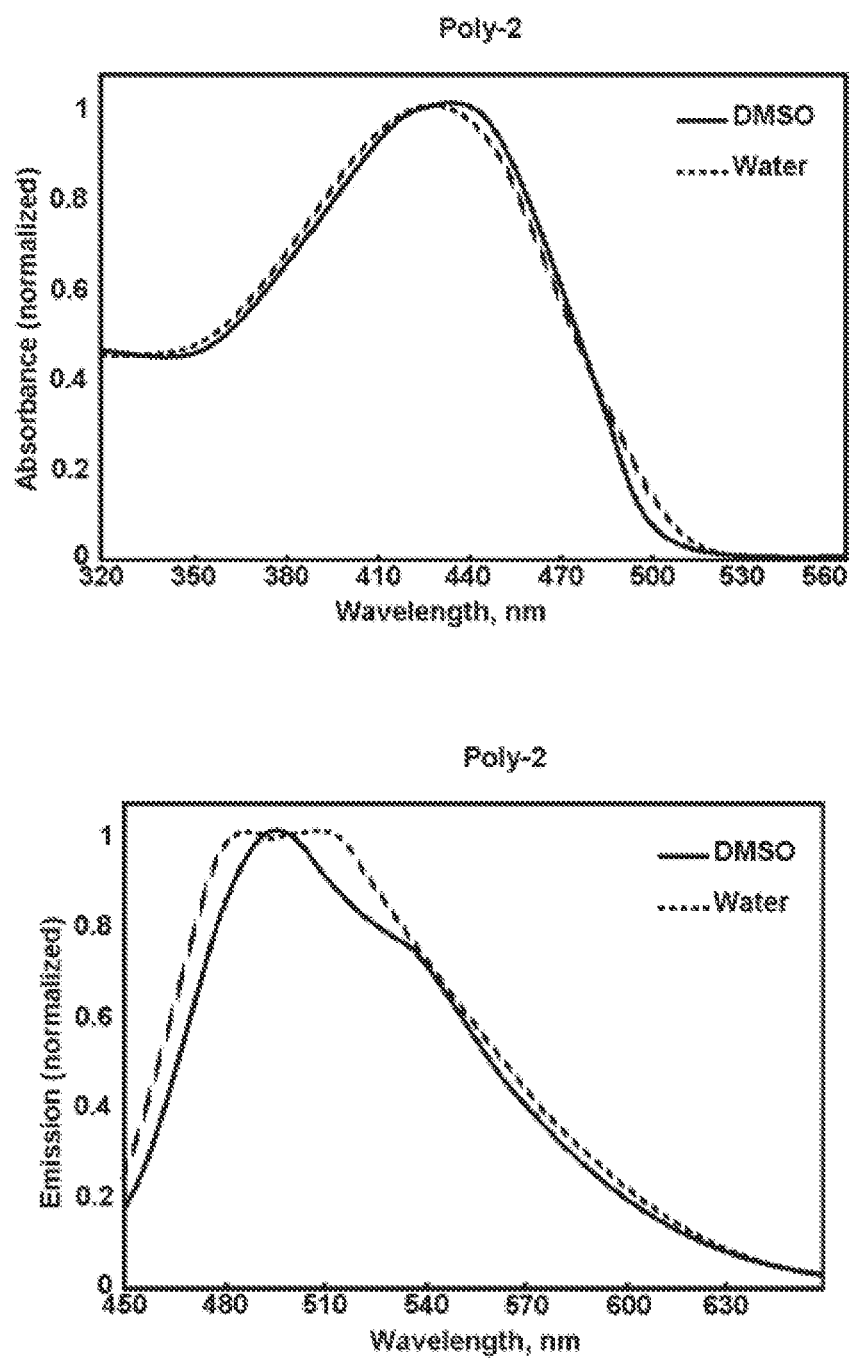
FIG. 6B shows UV absorbance (left) and emission (right) spectra of Poly-2 in DMSO and 95% water/5%DMSO.
Figure 7A:
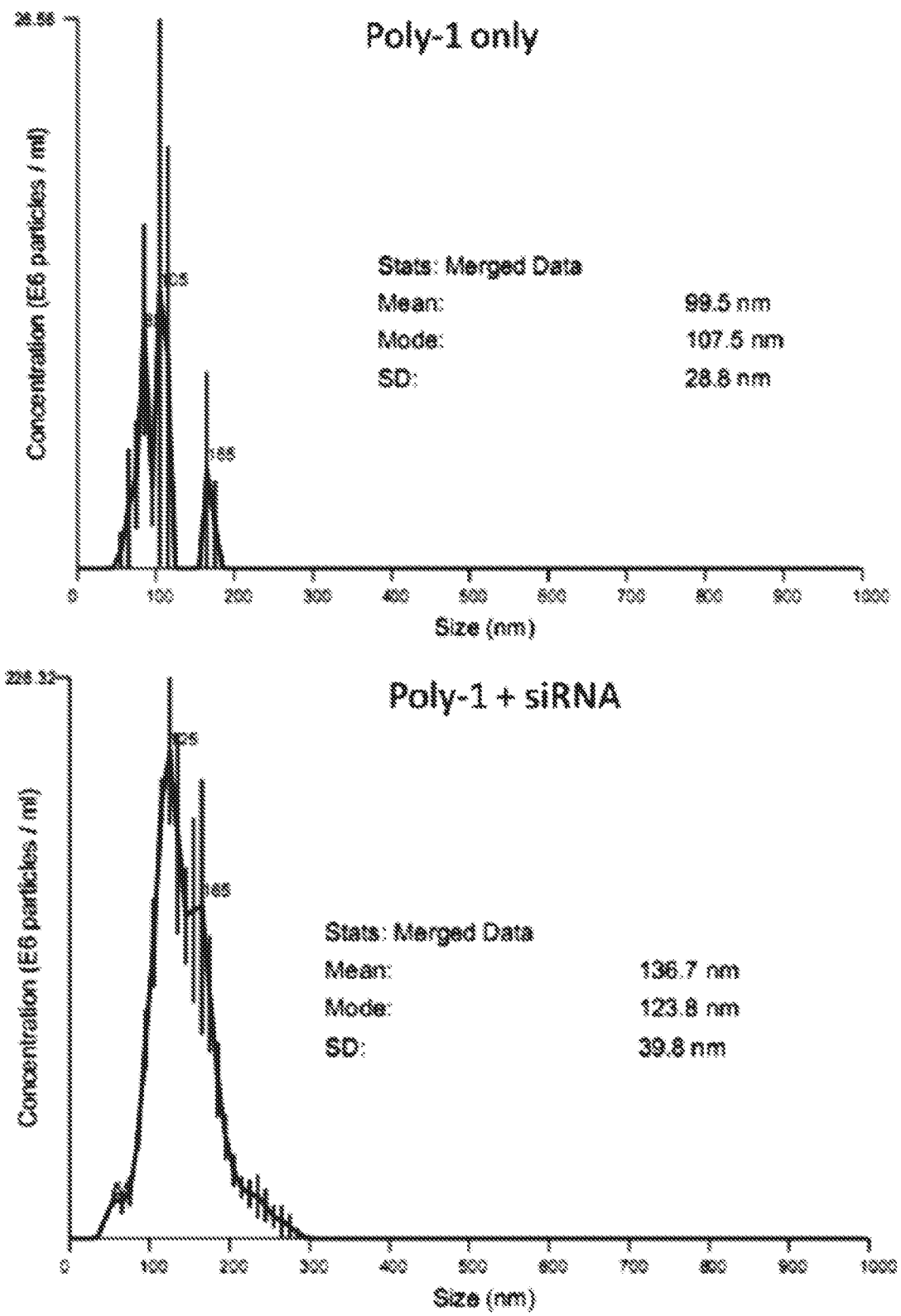
FIG. 7A shows a nanoparticle tracking analysis (NTA) of Poly-1.
Figure 7B:
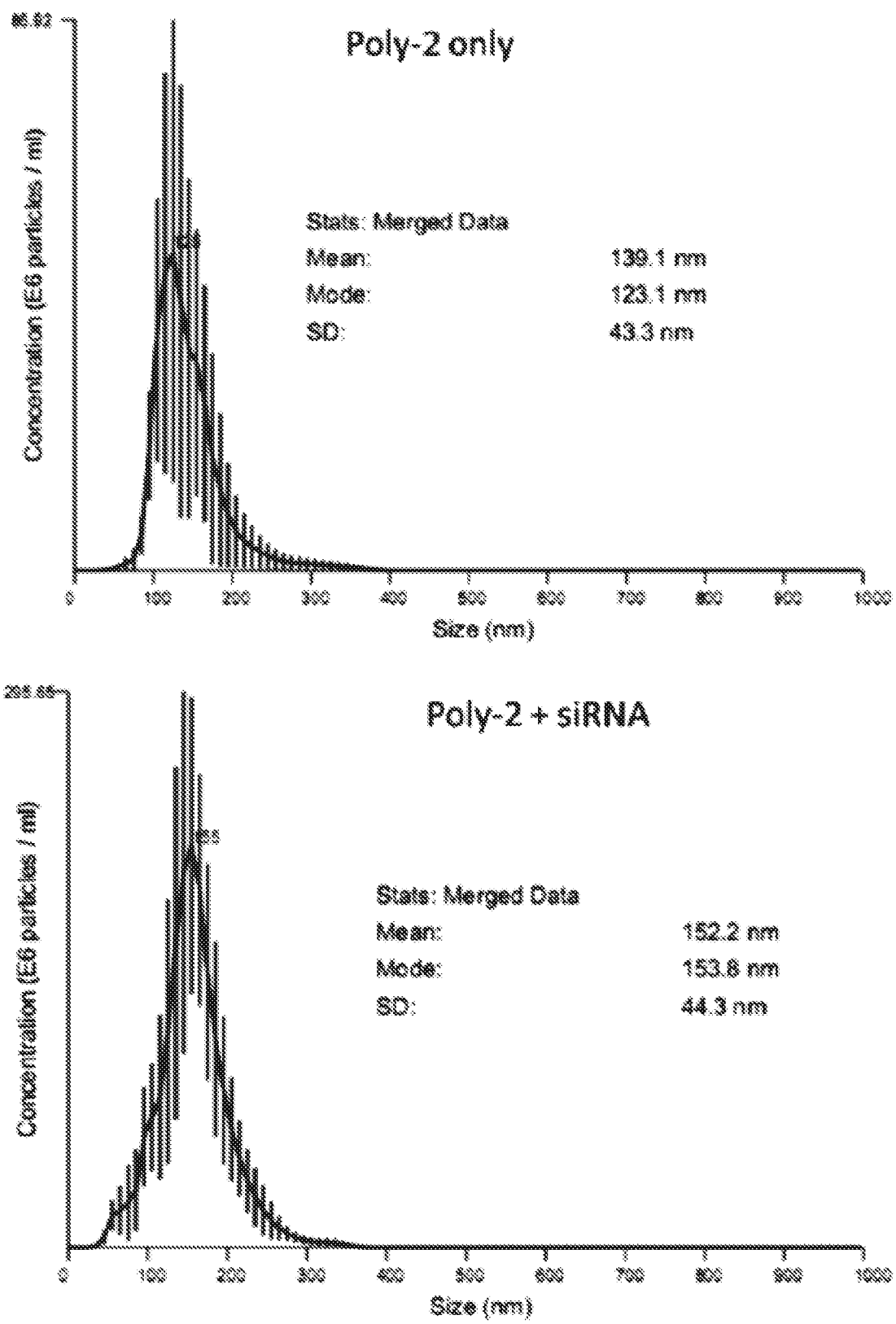
FIG. 7B shows a NTA of Poly-2.
Figure 8A:
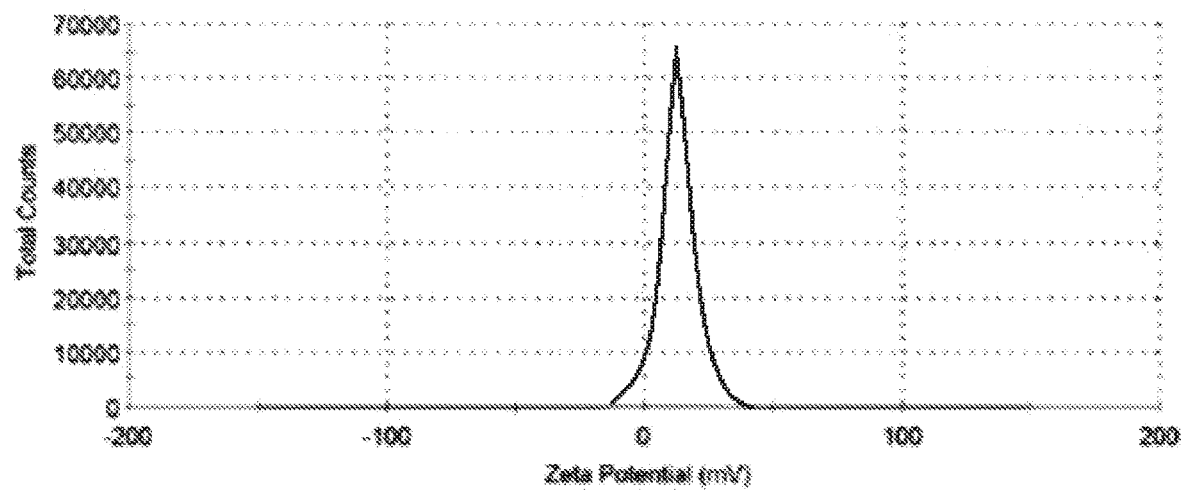
FIG. 8A shows a plot of zeta potential for Poly-1 with siRNA.
Figure 8B:
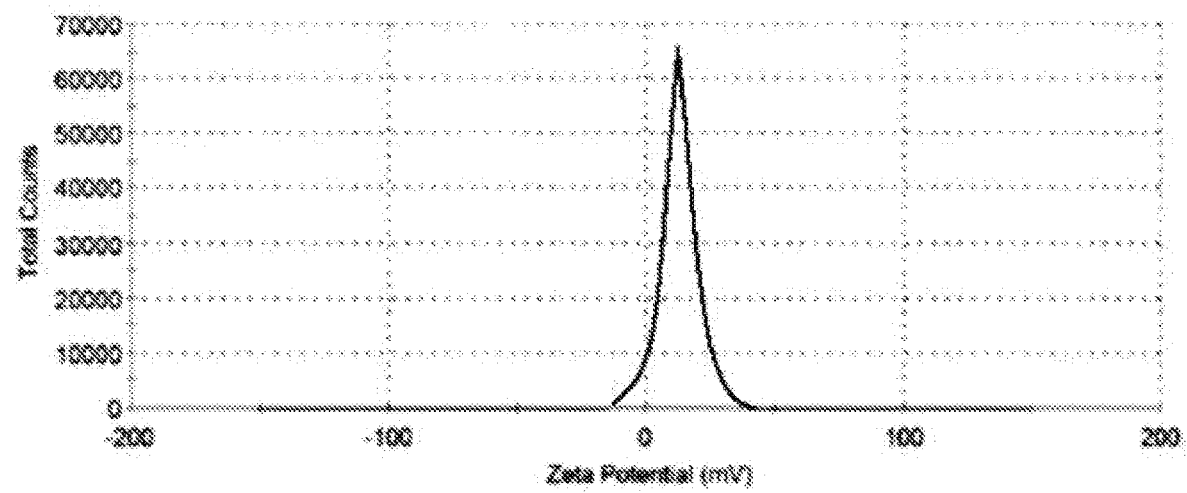
FIG. 8B shows a plot of zeta potential for Poly-2 with siRNA.

Hydrophilic PEG-like functional groups are introduced at the positive charge by reacting Boc-protected guanidine with aminoethoxyethanol followed by Boc deprotection as shown in FIG. 5. According to an embodiment of the invention, Poly-2 of FIG. 5 is successfully synthesized in high yields, with formation of a guanylurea group in every repeating unit, as characterized by an amide proton signal in $^1$H-NMR spectra at about 12.3 ppm. Poly-2 exhibits good solubility in common organic solvents, characteristic absorption/emission profiles of CPs, as shown in FIGS. 6A and 6B, and has about a three-fold greater fluorescent quantum yield than Poly-1. Poly-1 and Poly-2 exhibit very weak dynamic light scattering signals even at concentrations in excess of the mM levels, implying that the non-aqueous soluble CPs are relatively well-solvated due to the highly charged guanidine and guanylurea, preventing hydrophobic backbone aggregation. Upon complexation of the CPs with the negatively charged siRNA, nanometer-sized polymer/siRNA polyplexes are formed. The hydrodynamic diameters (HDs) of Poly-1 and 2 are 137±40 and 152±44 nm, respectively, as shown in FIGS. 7A and 7B. Zeta potentials of both polyplexes are slightly positively charged, about +13 mV, as shown in FIGS. 8A and 8B.

Figure 9:
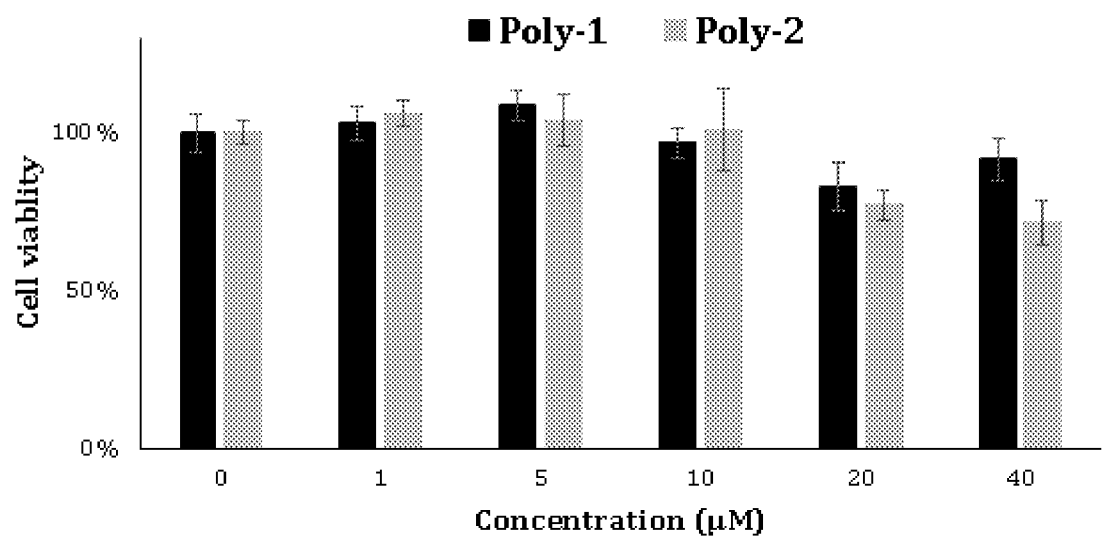
FIG. 9 shows a bar chart for Cell viability inhibition by Poly-1 and Poly-2.
Figure 10:
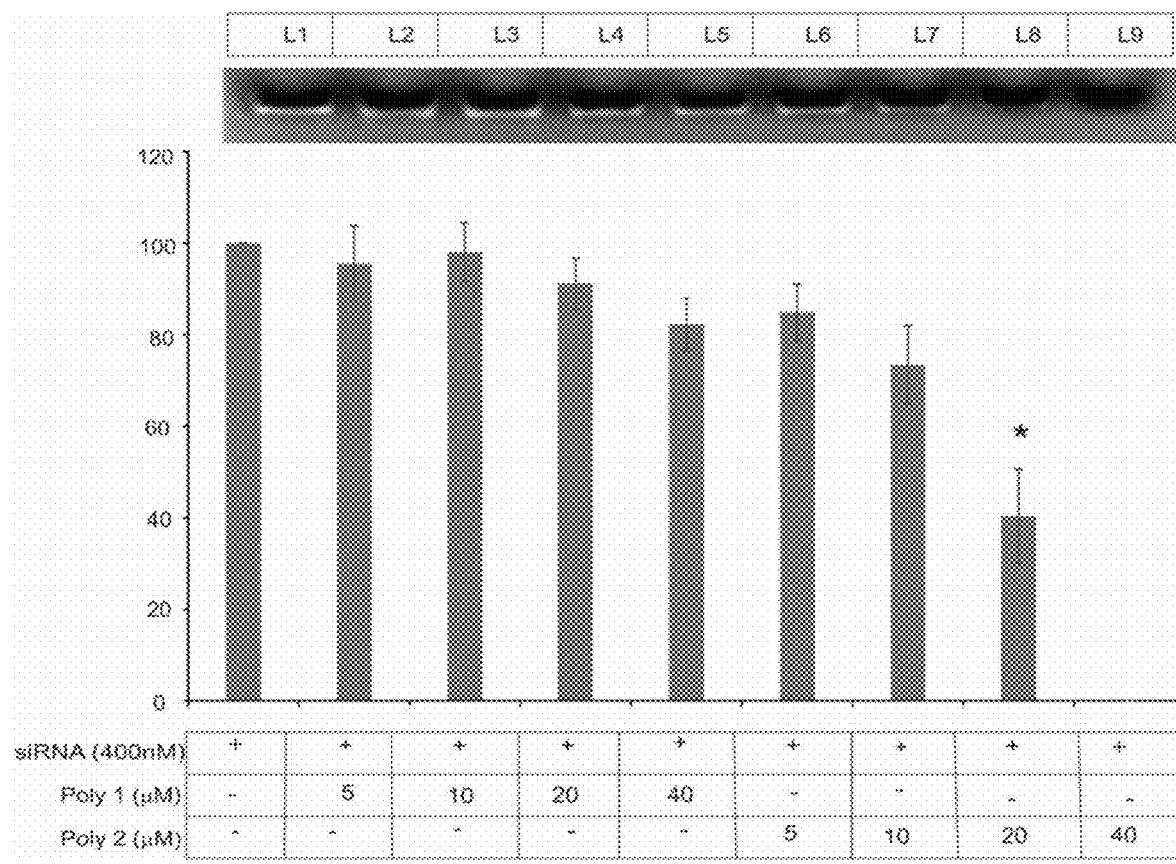
FIG. 10 shows a polyacrylamide gel electrophoresis retardation assay, top, where Lane 1: siRNA (400 nM); Lane 2: siRNA (400 nM) +Poly 1 (5 µM); Lane 3: siRNA (400 nM)+Poly 1 (10 µM); Lane 4: siRNA (400 nM) +Poly 1 (20 µM); Lane 5: siRNA (400 nM)+Poly 1 (40 µM); Lane 6: siRNA (400 nM)+Poly 1 (5 µM); Lane 7: siRNA (400 nM)+Poly 1 (10 µM); Lane 8: siRNA (400 nM)+Poly 2 (20 µM); and Lane 9: siRNA (400 nM)+Poly 2 (40 µM), where significance at p<0.05.

No cell viability inhibition was exhibit at up to 40 µM concentration of either Poly-1 or Poly-7, demonstrating that supporting the modulation at guanidine does not raise viability inhibition. As indicated in FIG. 9, the siRNA against histone deacetylase (HDAC) (siHDAC) was delivered by both Poly-1 and Poly-2 to BEAS-2B cell lines, where mRNA expression levels are quantified by RT-qPCR using glyceraldehye 3-phosphate dehydrogenase (GAPDH) as a control gene. By Gel retardation assay, as shown in FIG. 10, the guanylurea-functionalized Poly-2 exhibits much better siRNA complexation than the guanidine-containing Poly-1. The entire siRNA is complexed by Poly-2 at an N (nitrogen)/P (phosphate) ratio of about 5, whereas Poly-1 showed only complexes about 20% at that ratio.

Figure 11A:
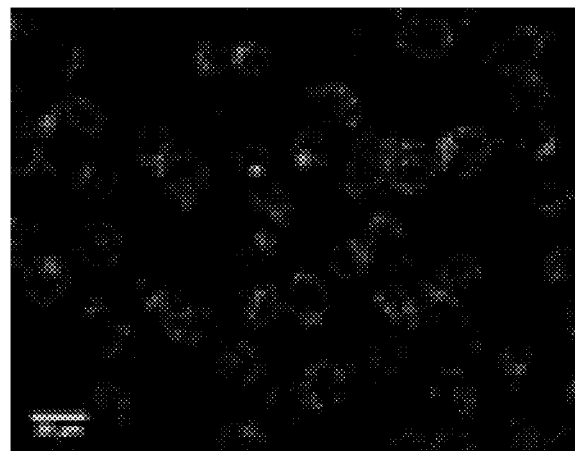
FIG. 11A shows a confocal microscopic image of BEAS-2B cells incubated with CP/siGLO polyplexes for 1 h show CP-mediated siRNA delivery for Poly-1 located in the cytosol having a green signal from the CP.
Figure 11B:
FIG. 11B shows a confocal microscopic image of REAS-2B cells incubated with CP/siGLO polyplexes of Poly-1 for 1 h where a red signals from siGLO is observed.
Figure 11C:
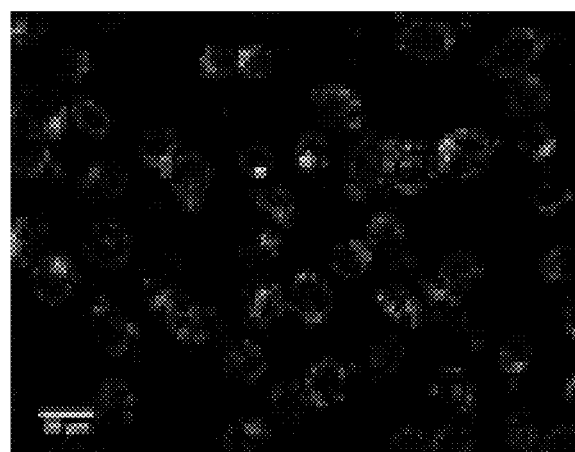
FIG. 11C shows a combined signal from the CP and siGLO in from cells treated with Poly-1 in a confocal microscopic image of BEAS-2B cells incubated with CP/siGLO polyplexes of Poly-1 for 1 h.
Figure 11D:
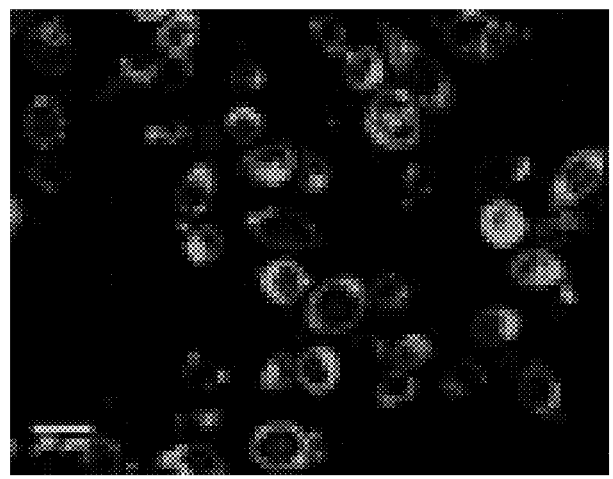
FIG. 11D shows a confocal microscopic image of BEAS-2B cells incubated with CP/siGLO polyplexes for 1 h show CP-mediated siRNA delivery for Poly-2 located in the cytosol having a green signal from the CP.
Figure 11E:
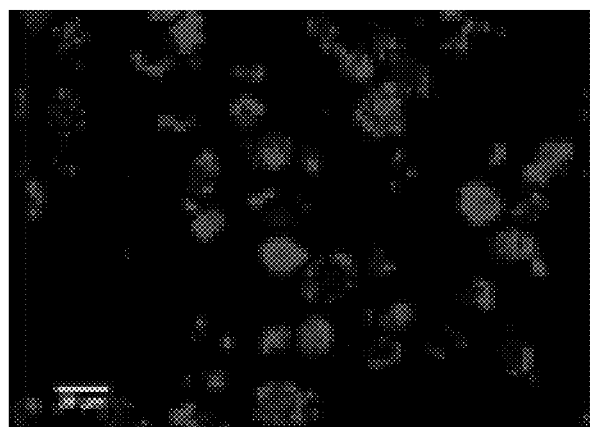
FIG. 11E shows a confocal microscopic image of BEAS-2B cells incubated with CP/siGLO polyplexes of Poly-1 for 1 h where a red signals from siGLO is observed.
Figure 11F:
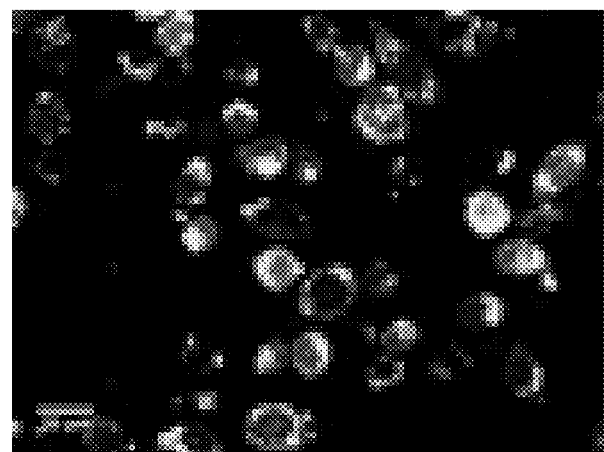
FIG. 11F shows a combined signal from the CP and siGLO in from cells treated with Poly-2 in a confocal microscopic image of BEAS-2B cells incubated with CP/siGLO polyplexes of Poly-1 for 1 h where a portion of siGLO were released from Poly 2 and localized in the nucleus.

Using a fluorescently labeled control siRNA (i.e., siGLO Red), CP-mediated siRNA delivery for Poly-1 and Poly-2 is confirmed by confocal microscopy, as shown in FIGS. 11A, 11B, and 11C and FIGS. 11D, 11E, and 11F, respectively. After an hour of incubation at the N/P ratio of about 9, the CPs and siGLO reside inside BEAS-2B cells. The relatively high amount of siGLO observed in cells incubated with Poly-2, indicates that guanylurea modification increases siRNA delivery efficiency. The strong siGLO complexation by Poly-2, results in higher amounts of intracellular siGLO due to enhanced cellular entry of the complex resulting from a balance of hydrophobicity and charge density. When the positive charge of guanidine is balanced with hydrophobic moieties, polymers with many guanidine-containing carriers exhibit efficient membrane interaction followed by high intracellular entry. A portion of siGLO is found in the nuclei of cells treated with Poly-2/siGLO, as indicated in FIGS. 11E and 11F; indicating siGLO is released from Poly-2. From this result, it appears that hydrophilic modification at the positive charge of CPs allows better siRNA complexation, efficient cellular entry, and subsequent intracellular release of siRNA.

The guanylurea-functionalized CP for delivery of siRNA, according to an embodiment of the invention, was evaluated in a physiological setting, where ex vivo primary bronchial epithelial cells were incubated with Poly-2/siGLO polyplex. Primary bronchial epithelial cells obtained from nasal turbinates or cadaver lungs were grown in plastic dishes or on porous supports at the air-liquid interface. While the cells grown on plastic dishes present a poorly differentiated squamous phenotype, the cells grown on porous supports at the air-liquid interface closely recapitulate their normal in vivo morphology, including: the cell-matrix and cell-cell interactions; differentiation of mucus, goblet, and ciliary cells; polarized epithelial ion transport; and regenerating the native bronchial epithelium ex vivo. Therefore, ex vivo primary human bronchial epithelial cells are an excellent model of the constituted airway epithelial and are used for ex vivo drug delivery studies before extrapolating to large animal models or human clinical studies.

Figure 12:
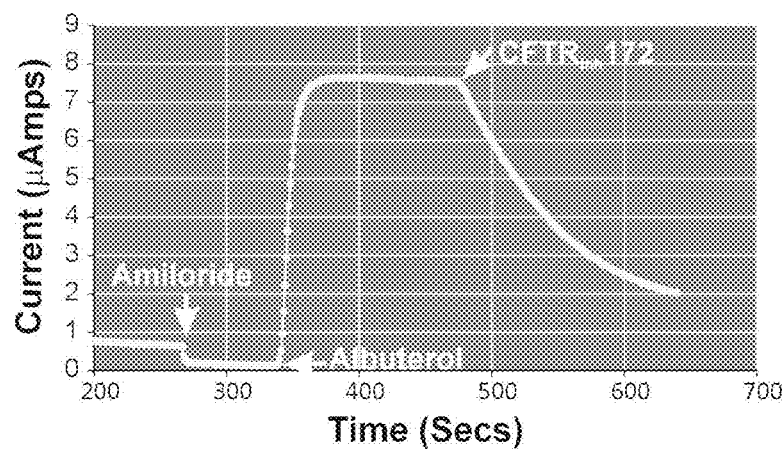
FIG. 12 shows a plot of polarization upon addition of a CFTR activator (albuterol to block the epithelial sodium channel) followed by an inhibitor ($CFTR_{inh}172$) to NHBE cells mounted in a Ussing chamber where a large apical current change with the cultured NHBE cells exhibiting the characteristic membrane polarization of epithelium.

Conformation of the polarity and integrity of the epithelium carried out by trans-epithelial electrical resistance (TEER) measured after 21 days of differentiation at the air-liquid interface, where primary NHBE cells exhibit a mean TEER value of 731 ohms/cm$^2$, indicating efficient barrier formation. The apical chloride ion flux, monitored by treatment with albuterol activates the cystic fibrosis transmembrane conductance regulator (CFTR) protein to stimulate chloride ion flux. As shown in FIG. 12, a sharp current increase occurs immediately upon addition of albuterol. The specificity of CFTR-mediated efflux is indicated by the decreased current after addition of a CFTR inhibitor (i.e., CFIR$_{inh}$172).

Confocal microscopic images clearly indicate that Poly-2 delivers siGLO to NHBE cells, while cells treated with Poly-1/siGLO and Lipofectamine/siGLO, respectively, exhibited only background signals. The added hydrophilic groups near the positive charges promote diffusion of the ionic complex through the mucus layer followed by efficient intracellular entry.

Figure 13:
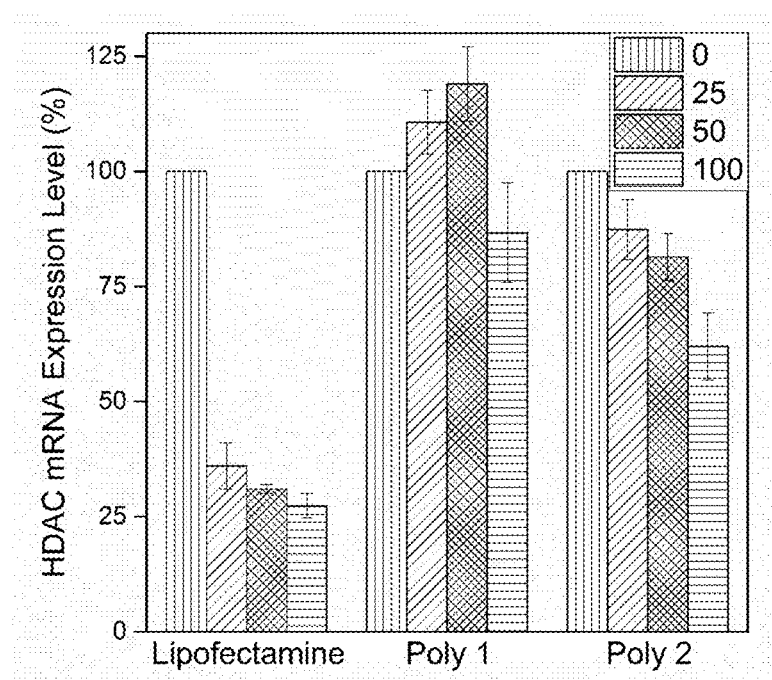
FIG. 13 is a bar chart of the HDAC mRNA knockdown efficiency in BEAS-2B cells for Lipofectamine, Poly-1 and Poly-2.
Figure 14:
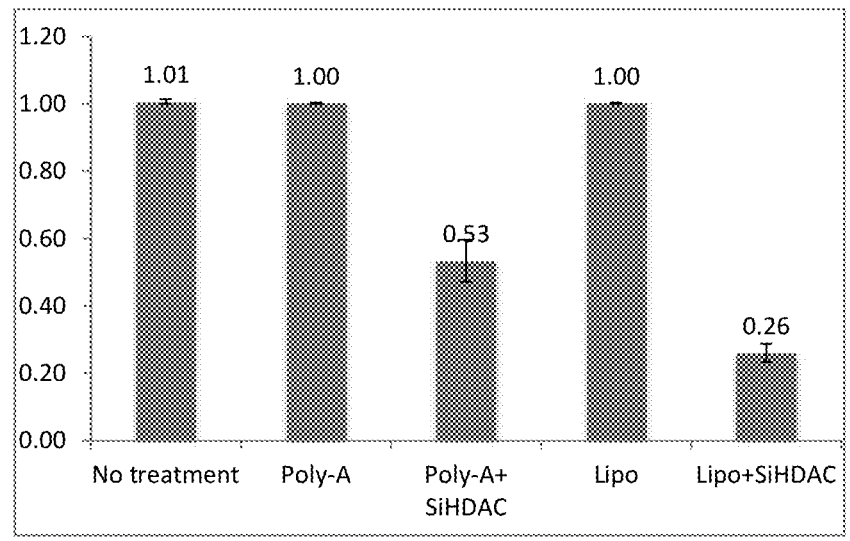
FIG. 14 is a bar chart of the relative knockdown efficiency of BEAS-2B cell treated with Poly-2/siHDAC, where Poly-A is Poly-2.
Figure 15:
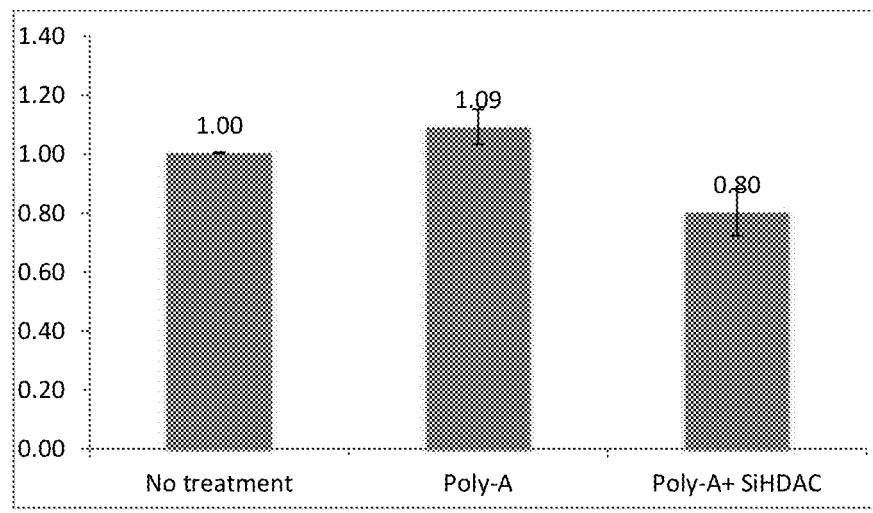
FIG. 15 is a bar chart of the relative HDAC mRNA expression level at primary NHBE cell treated with Poly2/siHDAC, where Poly-A is Poly-2.

The gene knockdown efficiency of Poly-2 was initially evaluated at the in vitro level using siRNA against histone deacethylase (HDAC) (siHDAC) in BEAS-2B cells. The mRNA expression levels were quantified by real time quantitative polymerase chain reaction (RT-qPCR) using glyceraldehye 3-phosphate dehydrogenase (GAPDH) as a control gene. Inhibition of HDACs has been shown to suppress proliferation of non-small-cell lung cancer (NSCLC) and restore the drug sensitivity to NSCLC. The guanidine-modified Poly-1 exhibits relatively poor knockdown efficiency even in immortalized cell lines. Poly-2 and Lipofectamine exhibit a dose-dependent target gene knockdown, supporting that the guanylurea modification enhances RNAi efficiency, as indicated in FIG. 13. As FIG. 14 indicates, Poly-2 exhibit sufficient knockdown of the target gene at the mRNA level and is comparable to Lipofectamine. The HDAC mRNA expression level at primary NHBE cell treated with Poly-2/siHDAC indicates knockdown, as shown in FIG. 15, whereas Lipofectamine does not knockdown the target gene.

Figure 16:
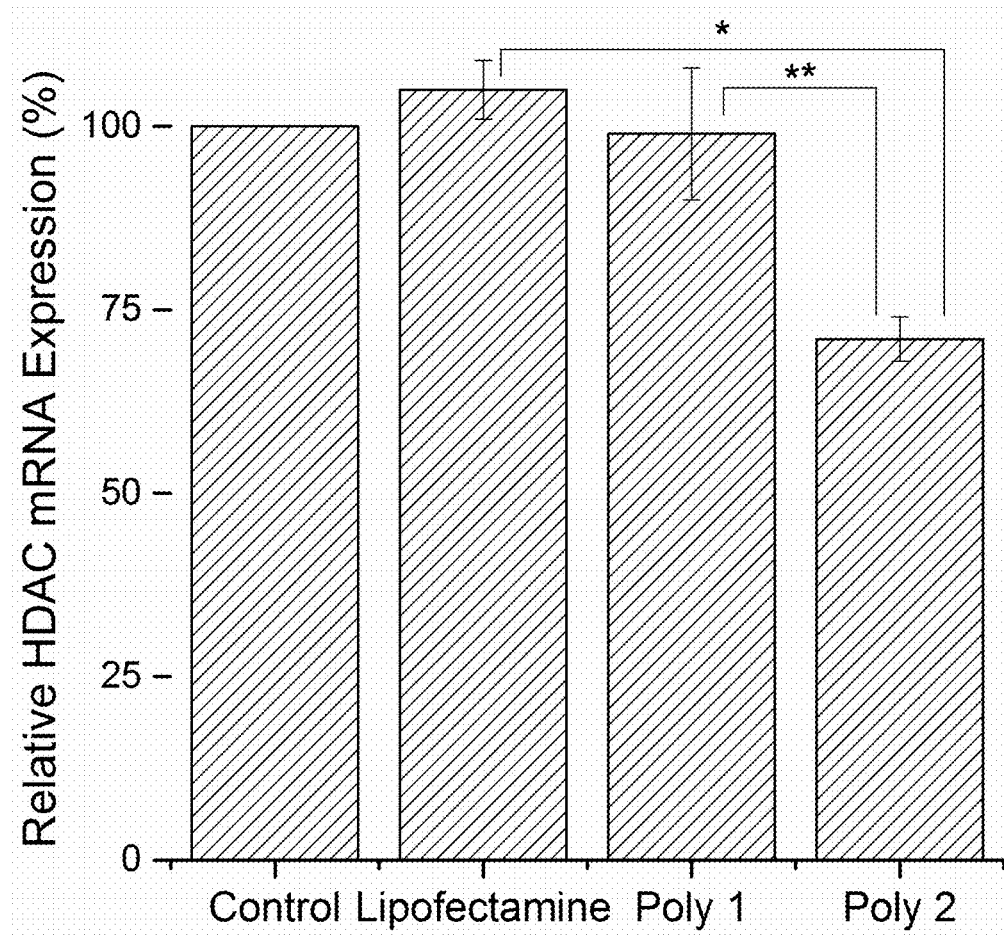
FIG. 16 is a bar chart of the relative HDAC mRNA expression levels of NHBE cells treated with Lipofectamine 2000 (a lipid-based), Poly 1 (cationic), and Poly 2 (with a modulated chemical environment at its positive charge), where *p<0.0003 and **p<0.007.

Both lipid-based and purely positively charged carriers, such as Poly-1, exhibit no or poor HDAC knockdown efficiency in well-differentiated NHBE cells, as shown in FIG. 16, due to poor cellular siRNA delivery to the epithelium cells. Meanwhile, Poly-2 consistently exhibits the average of about 30% knockdown efficiency over six independent lung samples. Due to the negatively charged hydrophobic mucus layers, positively charged Poly-1 and lipid-based carriers experience difficulty in diffusing through the mucus layer. The hydrophilic environment introduced at the positive charge of guanidine allows efficient ionic complexation and diffusion through the mucus layer.

Chemical modification of the guanidine group often destroys the function available for guanidine, where nitrogen atoms of guanidines, bearing electron-withdrawing substituents, act as a reactive nucleophile. Few methods for guanidine modification are known and they include the reaction between guanidine and alcohols under Mitsunobu reaction condition and alkylation of guanidine with electrophiles, such as alkyl halides, under basic conditions. Recently, Kessler et al. *Angew Chem Int Ed Engl.*, 2016, 55(4):1540-3 taught the modification of the guanidine group of Cilengitide ligand by N-methylation, N-alkylation, or N-acylation and successfully demonstrated an increasing selectivity of Cilengitide ligands. Takemoto et al. *J. Org. Chem.*, 2009, 74 (1), pp 305-11 taught the use of palladium- or iridium-catalysts and displayed a direct modification of guanidines. The direct modification of guanidine head group received much less attention and there are no reports of modification of guanidine moiety in polymer.

According to an embodiment of the invention, a catalyst free post polymerization reaction incorporates a variety of hydrophilic and hydrophobic functional group onto conjugated polymers (CPs). By this method, structurally diverse polymers are synthesized without tedious polymerization steps. The modified polymers are easily analyzed using NMR spectroscopy and are prepared with high yields overall. The guanidine head group reacts with diisopropylamine (DTPA), which yields a CP with solubility and physical properties that differ from the CP with the guanidine head group. Incorporation of hydrophobic groups, like piperidine, and hydrophilic group, like morpholine and aminoethoxyethanol, provide other CPS with varied properties.

Figure 17:
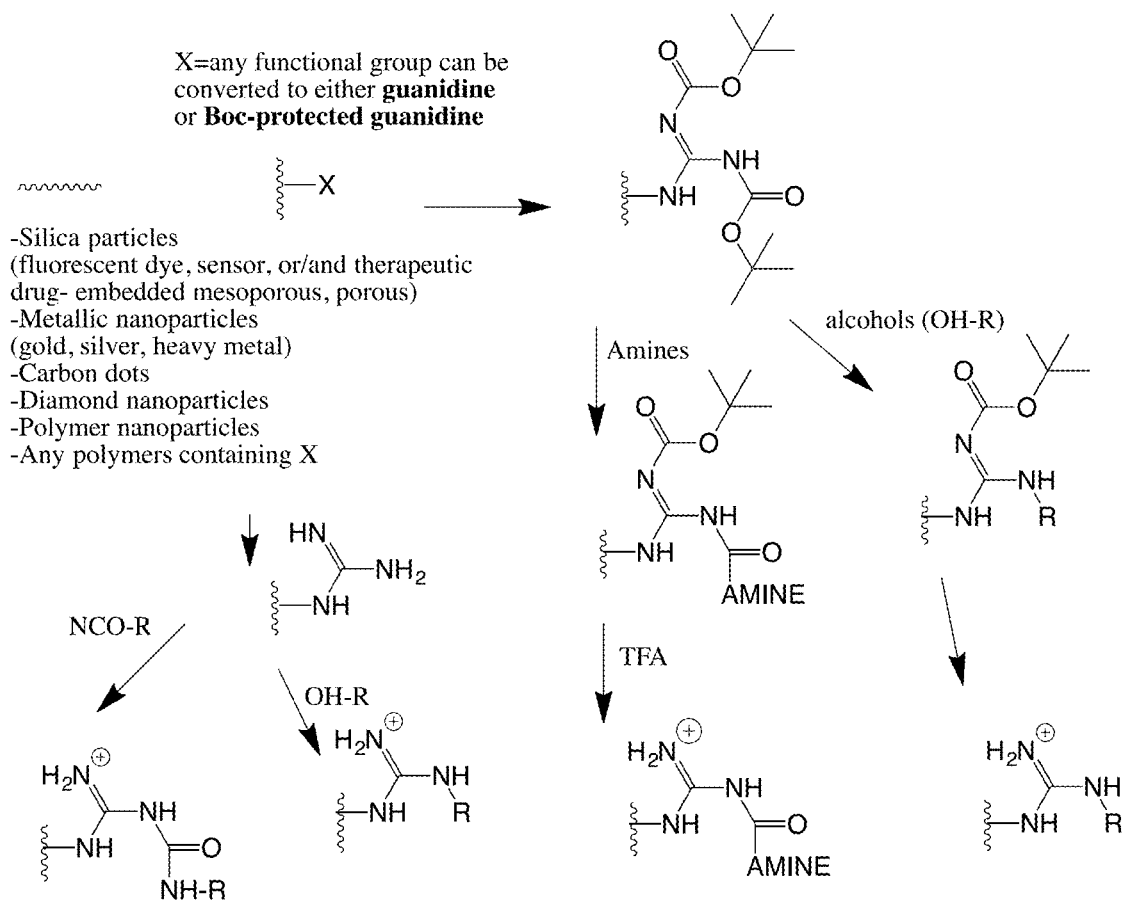
FIG. 17 shows a scheme for the various synthetic methods of formation of modulated guanidine functionalized nanoparticles or polymers, according to embodiments of the invention.

In embodiments of the invention, the polymer need not be a conjugated polymer, which is generally ridged, but can be a non-conjugated polymer that has a flexible backbone. In embodiments of the invention the polymer can have flexible side chains that enhance the water solubility of the polymer. In embodiments of the invention, the guanidine or protected guanidine is sufficient to impart water solubility. Synthetic and natural polymers that can be employed can be, but are not limited to, amine functionalized polymethacrylates and polyacrylates, branched and linear polyehtyleneimines, polyamidoamine, amine functionalized dendrimers, poly-L-lysine, chitosan, amine functionalized dextran, amine functionalized alginates, amine functionalized heparin, and amine functionalized oligo or polysacchnride, In embodiments of the invention, nanoparticles are used for efficient intracellular delivery and labeling after modulating surface properties to enhance their initial interaction following entry. As shown in FIG. 17, a nanoparticle bearing a surface functional group or a or polymer with a functional group can be converted by reaction at the functional group to a guanidine, Boc-protected guanidine, or any other protected guanidine. The nanoparticles can be those that are metal oxides, metal carbides, metal nitrides, metals, diamond, or any other type of nanoparticle. The polymer can be in the form of a soluble polymer or can be a nanoparticle where the functional groups are of sufficient concentration at the nanoparticle surface to yield a nanoparticle that is decorated with the guanidine, Boc-protected guanidine, or any other protected guanidine. The nanoparticles can be of a single structure or a core-shell particle. The particles can inherently have surface functionality that react with guanidine or protected guanidine. The particle surface can be functionalized by reaction with an agent, for example, a silane coupling agent, such as, but not limited to, 3-aminopropyltrimethoxy silane, or thiol or disulfide containing alkyls with hydroxyl or amine groups for functionalization of metal nanoparticles.

METHODS AND MATERIALS

Materials

Reagents and solvents were purchased from Fisher Scientific and used without further purification. Deuterated solvents were purchased from Cambridge Isotope Laboratories (Cambridge, Mass.). All solutions were prepared using deionized (DI) water (-18%2) from water purification system (Ultra Purelab system, ELGA/Siemens). The number average molecular weight ($M_n$), weight average molecular weight (M), and polydispersity index (PDI=Mw/Mn) of CPs were determined by gel permeation chromatography (GPC) against polystyrene standards using a Shimadzu high performance liquid chromatography (HPLC) system fitted with PLgel 5 μm MIXED-D columns and SPD-20A ultraviolet-visible (UV-vis) detector at a flow rate of 1.0 mL/min. Samples for GPC, small amount (~100 μL) of polymer in dimethylformamide (DMF) or dichloromethane (DCM) was diluted with 1 mL of HPLC grade THF and then filtered through a 0.45 μM polytetrafluoroethylene (PTFE) syringe filter prior injection. UV-vis spectra were recorded using a Varian Cary 50 Bio spectrophotometer. Fluorescence spectra were obtained using a FluoroLog-3 Spectrofluorometer (Jobin Yvon/Horiba). 9,10-diphenylanthracene (QY=0.9) in cyclohexane was used as a fluorescence standard. Fourier transfoon infrared (FTIR) spectra were recorded on a Perki-nElmer Spectrum 100 FTIR Spectrometer. Fine polymer powders were directly mounted on an attenuated total reflection (ATR) cell of the spectrometer. Nuclear magnetic resonance (NMR) spectra were recorded on a 400 MHz Avance Bruker NMR spectrometer. Chemical shifts were reported in parts per million (ppm) for 1H NMR on the δ scale based on the middle peak (δ=2.50 ppm) of the dimethylsulfoxide (DMSO-d6) solvent as an internal standard.

Monomer Synthesis

Synthesis of monomer A. Guanidinium-containing aryl-diiodide monomer A was synthesized as described in Ahmed et al., *Bioconjugate Chem.* 2018, 29 (4), 1006-9.

Synthesis of monomer B. A round-bottomed flask was charged with compound A (2.00 g, 1.96 mmol), trimethyl-silylacetylene (0.77 g, 7.84 mmol), $PdCl_2(PPh_3)_2$ (137.6 mg, 0.20 mmol), and CuI (18.6 mg, 0.10 mmol). The round-bottomed flask was evacuated and filled with $N_2$ three times. A solution of tetrahydrofuran (THF) and diisopropylamine (DIPA) was mixed in a 4:1 ratio (v/v) and degassed with $N_2$ for 10 minutes, and then 50 mL was transferred to the ROUND-BOTTOMED FLASK via a cannula. The reaction mixture was stirred at room temp for 3 h equipped with a $N_2$ balloon. The yellow reaction mixture was filtered to remove insoluble particles and THF was distilled from the mixture in vacuo. The reaction mixture was dissolved in DCM and washed with 1M $NH_4Cl$ two times followed by brine. Column chromatography using 30% ethyl acetate in hexane yielded a trimethylsilyl (TMS)-protected compound as a white solid (1.22 g, 65% yield). NMR (400 MHz), $CDCl_3$, δ: 11.46 (s, 0.95H), 8.67 (s, 0.96H), 7.21 (s, 0.98H), 4.1 (t, J=4.4 Hz, 2H), 3.88 (t, J=4.8 Hz, 2.H), 3.78 (t, J=4.8 Hz, 2H), 3.66 (q, J=5.2 Hz, 2H), 1.50 (s, 9.111), 1.45 (s, 9.21H), 0.10 (s, 18.2H).

In a round-bottomed flask, the trimethylsilyl (TMS)-protected compound (1.00 g, 1.04 mmol), and potassium carbonate (0.36 g, 2.60 mmol) were mixed in methanol (40 mL). The round-bottomed flask was then stirred at r.t. for 20 min. Upon confirmation of TMS deprotection by TLC, the solvent was dried in vacuo. The reaction mixture was then purified by short-path column chromatography using 35% ethyl acetate in hexane, yielding a yellowish solid (0.51 g, 60% yield). $^1H$ NMR (400 MHz), $CDCl_3$, δ: 11.45 (s, 1H), 8.67 (s, 1H), 6.98 (s, 1H), 4.15 (t, J=4.4 Hz, 2H), 3.86 (t, J=4.8 Hz, 2H), 3.75 (t, J=4.8 Hz, 2H), 3.65 (q, J=5.2 Hz, 2H), 3.35 (s, 1H), 1.50 (s, 9H), 1.45 (s, 9H). $^{13}C$ NMR (400 MHz), $CDCl_3$, δ: 156.4, 154.2, 153.1, 118.3, 113.8, 83.2, 83.1, 79.6, 79.4, 70.0, 69.8, 69.4, 40.9, 28.4, 28.2. FT-1R (neat): 3330.9, 3281.4, 2975.3, 2930.5, 1720.2, 1636.1, 1613.1, 1568.2, 1495.8, 1410.3, 1319.7, 1222.7, 1129.0, 1049.9 $cm^{-1}$ FIRMS $[M+H]^+$=817.4342 (theoretical) and 817.4365 (observed).

Guanidine Homo Polymer (Boc-Protected Poly-1)

Figure 18:
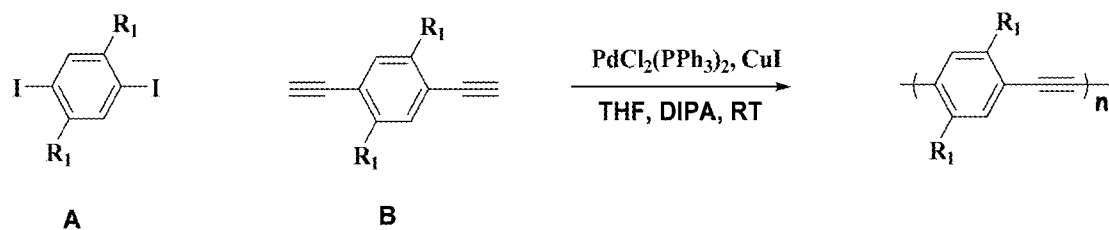
FIG. 18 shows a reaction scheme for the preparation of a G-CP.
Figure 18:
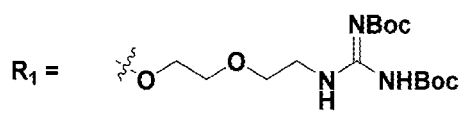

As indicated in the reaction scheme of FIG. 18, a Schlenk flask was charged with guanidine substituted p-diiodiaromatic monomer A 50 mg, 0.04 mmol, guanidine substituted p-diacetylenodiaromatic comonomer B (40.0 mg, 0.04 mmol), $PdCl_2(PPh_3)_2$ (3.43 mg, 0.005 mmol), and CuI (0.47 mg, 0.0024 mmol). The Schlenk flask was evacuated and filled with $N_2$. A solution of tetrahydrofuran (THF) and diisopropylamine (DIPA) was mixed in 4:1 volume ratio and degassed with $N_2$, and 2 mL was transferred to the Schlenk flask via a cannula. The reaction mixture was stirred at RT for 16 h. The solution was filtered through a glass wool filter and added dropwise to methanol to precipitate the GCP. The supernatant was decanted; the precipitate was re-dissolved in dichloromethane (0.5 mL) and purification method was repeated using methanol. The resulting Boc protected polymer in DCM was characterized by gel permeation chromatography (GPC) and their absorption/emission profile was measured. The final polymer was allowed to dry under high vacuum for 16 h before $^1$H NMR characterization. $^1$H NMR (400 MHz), $CDCl_3$, δ: 11.46 (s, 1H), 8.62 (s, 1H), 7.05 (s, 1H), 4.24 (s, 2H), 3.91 (s, 2H), 3.74 (s, 2H), 3.62 (s, 2H), 1.48 (s, 9H), 1.45 (s, 9H). FT-IR (neat): 3329.4, 3131.7, 2975.3, 2931,3, 1720.1, 1635.2, 1614.0, 1567.7, 1503.9, 1411.8, 1364.5, 1319.8, 1280.5, 1249.7, 1131.0, 1048.8 $cm^{-1}$ GPC: Mn=13,500 g/mol, Mw=18,000 g/mol, PDI=1.30, UV-Vis (THF) $\lambda_{max}$=442 nm, Fluo $\lambda_{max}$=469 nm.

Guanidine-DIPA (PG-D)

Figure 19:
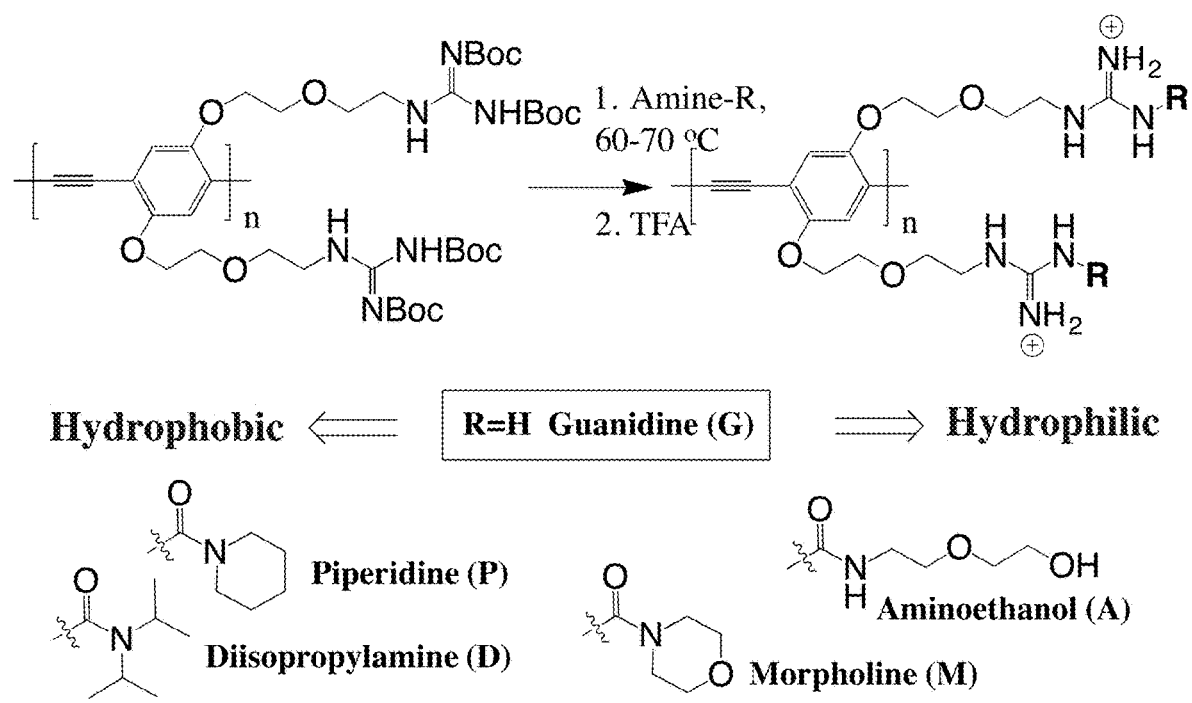
FIG. 19 shows a reaction scheme for the preparation of a modulated G-CP, according to an embodiment of the invention.

As illustrated in FIG. 19, using the general polymerization procedure for Boc-protected Poly-1, above, through the addition of the 4:1 THF/DIPA mixture a latent reaction mixture was formed with the Boc-protected Poly-1. The reaction mixture was heated at 80° C. for 16 h. Upon precipitation, as above, an overall yield of 63% (26.9 mg) was achieved. The resulting polymer in DCM was characterized by gel permeation chromatography (GPC) and its absorption/emission profiles were measured. The final polymer was allowed to dry under high vacuum for 16 h before $^1$HNMR characterization.

$^1$H NMR (400 MHz), $CDCl_3$, δ: 12.42 (s, 0.92H), 8.21 (s, 0.88H), 7.05 (s, 0.88H), 4.23 (s, 2H), 3.90 (s, 2H), 3.75 (s, 3.46H), 3.60 (s, 0.61H), 3.54 (s, 1.92H), 1.42 (s, 9.23H), 1.23 (s, 12.25H) GPC: Mn=13155 g/mol, Mw=22363 g/mol, PDI=1.70, UV-Vis (THF) $\lambda_{max}$=434 nm, Fluo $\lambda_{max}$=472 nm.

Boc-deprotection to Poly-1

A solution of Boc-protected Poly-1 in DCM (1.00 mL) was treated with trifluoroacetic acid (TFA) at room temperature for 48 hours. The solvent was removed under reduced pressure and the crude material was dissolved in minimum amount of dimethylformamide (DMF) to have a clear homogeneous solution. The polymer solution in DMF was transferred to diethyl ether, resulting in yellowish fiber like precipitates that were collected by decantation. The polymer was dissolved in DMF and then re-precipitated in ethyl acetate (EA). This process was repeated twice and the final Boc-deprotected polymer was collected by decantation followed by vacuum dry. After drying in a high vacuum, the final deprotected polymer was a yellow gel (74.6% yield) with complete Boc-deprotection confirmed by $^1$H NMR. $^1$H NMR (400 MHz, DMSO-$d_6$, δ): 8.13 (s, 1H), 7.92 (s, 2H), 7.27 (s, 2H), 6.87 (s, 1H), 5.77 (s, 1H), 5.03 (s, 1H), 4.30 (s, 2H), 3.98 (s, 2H), 3.59 (s, 4H), 3.50 (m, 6H), 2.98 (m, 10H), 2.87 (s, 1H), 2.01 (m, 6H). FT-IR (neat): 3360.36, 2160.37, 1736.79, 1681.18 $cm^{-1}$. UV-Vis (DMSO) $\lambda_{max}$=434 nm, Fluo $\lambda_{max}$=490 nm, QY=0.08.

Guanidine-Morpholine (PG-M)

A Schlenk flask was charged with GCP (10 mg, 0.012 mmol) and Morpholine (2.57 mg, 0.03 mmol). The Schlenk flask was evacuated and filled with $N_2$. A degassed tetrahydrofuran (THF) (1.5 mL) was transferred to the Schlenk flask via a cannula. The reaction was stirred at 80° C. for 16 h. The viscous polymer solution was filtered through glass wool followed by precipitation in diethyl ether and re-precipitating in methanol. The final polymer was yellow gel (7.72 mg with 76% yield). $^1$H NMR (400 MHz), $CDCl_3$, δ: 12.2 (s, 1H), 8.3 (s, 1.05H), 7.04 (s, 0.94H), 4.22 (s, 2H), 3.90 (s, 2.30), 3.74 (s, 4.47H), 3.60 (s, 4.06H). 3.52 (s, 4.21H), 1.42 (s, 9.90H). GPC: Mn=12364 g/mol, Mw=18598 g/mol, PDI=1.50. UV-Vis min $\lambda_{max}$=428 nm, Fluo $\lambda_{max}$=469 nm.

Guanidine-Piperidine (PG-P)

A Schlenk flask was charged with GCP (10 mg, 0.012 mmol) and Piperidine (2.51 mg, 0.03 mmol). The Schlenk flask was evacuated and filled with $N_2$. Degassed tetrahydrofuran (THF) (1.5 mL) was transferred to the Schlenk flask via a cannula. The reaction was stirred at 80° C. for 16 h. The viscous polymer solution was filtered through glass wool followed by precipitation in diethyl ether and re-precipitating in methanol. The final polymer was yellow gel (5.36 mg with 53% yield). $^1$H NMR (400 MHz), $CDCl_3$, δ: 12.30 (s, 0.98H), 8.22 (s, 0.91H), 7.05 (s, 0.86H), 4.22 (s, 1.92H), 3.90 (s, 1.99H), 3.74 (s, 2.15H), 3.65 (s, 2.42H), 3.59 (s, 0.83H), 3.53 (s, 1.78H), 3.47 (s, 2.71H) 1.42 (s, 911). GPC: Mn=14606 g/mol, Mw=27751 g/mol, PDI=1.90. UV-Vis (THF) $\lambda_{max}$=436 nm, Fluo $\lambda_{max}$=461 nm.

Guanidine-Aminoethoxyethanol (Poly-1)

A Schlenk flask was charged with Guanidine Homo Polymer (10 mg, 0.012 mmol) and Aminoethoxyethanol (3.1 mg, 0.03 mmol). The Schlenk flask was evacuated and filled with $N_2$. A degassed tetrahydrofuran (THF) (1.5 mL) was transferred to the Schlenk flask via a cannula. The reaction was stirred at 80° C. for 16 h. The viscous polymer solution was filtered through glass wool followed by re-precipitation in diethyl ether and re-precipitating in methanol. The final polymer was yellow gel (8.5 mg with 82.5% yield). $^1$H NMR (400 MHz), $CDCl_3$, δ: 12.05 (s, 0.73H), 8.27 (s, 0.63H), 7.04 (s, 0.87H), 6.03 (s, 0.55H), 4.22 (s, 2H), 3.90 (s, 2.38H), 3.72 (s, 5.42H), 3.53 (s, 8.26H), 3.36 (s, 02.31H), 1.42 (s, 7.22H); $^1$H NMR (400 MHz, DMSO-$d_6$, δ): 10.03 (s, 1H), 9.25 (s, 1H), 8.60 (s, 2H), 7.53 (s, 2H), 4.38 (s, 114), 4.03 (s, 1H), 3.81 (s, 2H). GPC: Mn=13767 g/mol, Mw=19529 g/mol, PDI=1.41. UV-Vis (THF) $\lambda_{max}$=435 nm, Fluo $\lambda_{max}$=465 nm; UV-Vis (DMSO) $\lambda_{max}$=434 nm, Fluo $\lambda_{max}$=494 nm, QY=0.20.

Physical and Photophysical Properties of CPs

For the data tabulated in Table 1, below, the UV absorbance and emission spectra of Poly-1 and Poly-2 were determined in DMSO and 95% water+5% DMSO. In a good solvent, such as DMSO, polymer absorbance and emission did not change. But in a poor solvent, such as water, their emission spectra were significantly changed. FIGS. 6A and 6B show the UV absorbance and emission spectra. The HD and zeta potential of Poly-1 and Poly-2 were determined using Nanoparticle Tracking Analysis (NTA) and Dynamic Light Scattering (DLS), respectively. For NTA and DLS, all cuvette, pipette, and pipette tips were autoclaved. The working area was cleaned with 70% ethanol to avoid cross contamination. Stock polymer samples were prepared at a concentration of 100 μM in DMSO solvent. 10 μL of a stock polymer solution in DMSO was added to 90 μL of RNAse water. The polymer solution in DMSO-water added to 11.11 nM and 900 μL siRNA containing RNAse water. The mixture of polymer and siRNA solution was gently pipetted, and 1 mL sample solution was then injected to the NTA chamber, and images of scattering particles in the sample were collected for 90 seconds. Software identified each individual particle and tracked its motion throughout the duration of the recorded video. The measured particle displacement is a function of Brownian motion, which is related to the particle size through the Stokes-Einstein equation. The final data was collected under the detection threshold at 4, to obtain the acceptable data meeting the concentration requirements. All measurements were performed in triplicate at 25° C. using a temperature controller. The values in Table 2, below, are averaged from three independent measurements. Selected representative NTA graphs are presented in FIGS. 7A and 7B.

TABLE 1

Physical and Photophysical Properties of CPs

| Poly | Mn[a] | PDI[b] | n[c] | $\Lambda_{max, abs}$ (nm)[d] | $\Lambda_{max, em}$ (nm)[d,e] | Zeta Potental, mV[f] | HD, nm[g] | QY[h] |
|---|---|---|---|---|---|---|---|---|
| 1 | 13,500 | 1.30 | 16 | 434 | 490 | 8.0 ± 2.0 | 99 ± 29 | 8.0 |
| 2 | 13,800 | 1.40 | 15 | 434 | 494 | 4.0 ± 1.0 | 139 ± 43 | 20 |

[a]Determined by gel permeation chromatography in THF,
[b]Polvdispersity index (Mw/Mn),
[c]Degree of polymerization,
[d]Measured in DMSO,
[e]Excitation wavelength 430 nm,
[f]Zeta potential in water,
[g]Determined by nanoparticle tracking analysis,
[h]Quantum yield in DMSO measured relative to diphenylanthracene standard

TABLE 2

Size in nm of Poly-1 and Poly-2 with siRNA

| Poly | Polymer, nm[a,b] | Polymer-siRNA, nm[a,b] |
|---|---|---|
| 1 | 99 ± 29 | 137 ± 40 |
| 2 | 139 ± 43 | 152 ± 44 |

[a]DMSO (1%) and water (99%),
[b]Conc. of final polymer and siRNA were 1 μM and 10 nM, respectively Zeta potentials of Poly-1 and Poly-2 in complexation with siRNA were measured using Zetasizer Nano-ZS (Zen 3600, Malvern Instruments Ltd.). The viscosity and refractive index of water were used for estimation of relative zeta potential difference among the samples. Stock polymer samples were prepared at a concentration of 1000 μM in DMSO. 10 μL of stock polymer solution was dissolved in 90 μL RNAse water. Then the polymer solution in RNAse water was transferred to 900 μL of siRNA containing RNAse water (siRNA concentration 11.11 nM) and the solution was mixed by pipetting. The final polymer and siRNA concentration in the solution were 10 μM and 100 nM, respectively. All measurements were performed in triplicates at 25° C. and the average values were reported in Table 3, below.

TABLE 3

Zeta potential of Poly-1 and Poly-2 with siRNA

| Poly | Polymer, mV[a] | Polymer-siRNA, mV[b] |
|---|---|---|
| 1 | 8.0 ± 2 | 11 ± 1.3 |
| 2 | 4.0 ± 1 | 12 ± 0.8 |

[a]DMSO (1%) and water (99%),
[b]Conc. of final polymer and siRNA were 1 μM and 10 nM Cell culture Primary human bronchial epithelial cells were isolated and re-differentiated at the air-liquid interface cultures as per Unwalla et al. Am. J. Respir. Cell. Mol. Biol. 2012, 46(4), 551-8 and Unwalla et al. Am. J Respir. Cell. Mol. Biol. 2015, 52 (1), 65-74. Cells were obtained from properly consented donors whose lungs were not suitable for transplantation for the causes unrelated to airway complications and supplied by University of Miami Life Alliance Organ Recovery Agency. Since the material was obtained from deceased individuals with minor, de-identified information, its use does not constitute human subjects research as defined by CFR 46.102. A signed and well documented consent of each individual or legal healthcare proxy for the donation of lungs for research purpose is on file with the Life Alliance Organ Recovery Organization allows research purpose of this material. Unless otherwise indicated, experiments used cells from non-smokers to not confound the findings in unknown ways. These primary cultures undergo mucociliary differentiation at the air-liquid interface reproducing in vivo morphology and key physiologic processes to recapitulate the native bronchial epithelium ex vivo. Primary NHBE cells isolated from human lungs were provided by University of Miami Life Alliance Organ Recovery Agency and re-differentiated on porous supports at the air-liquid interface. Re-differentiated NHBE cells were tested for ciliation by staining acetylated tubulin.

The immortalized normal human bronchial epithelial cell line BEAS-2B (ATCC CRL-9609) was purchased from the American Type Culture Collection (Manassas, Va., USA). BEAS-2B cells were cultured in BioLite 75 $cm^2$ flasks (Thermo Scientific) containing Bronchial Epithelial Cell Growth Medium (BEGM). BEGM media was supplemented with 0.1% (v/v) human recombinant epidermal growth factor, 0.1% (v/v) insulin, 0.1% (v/v) hydrocortisone, 0.1% (v/v) ethanolamine, 0.1% phosphoryl ethanolamine, 0.1% (v/v) retinoic acid, 0.1% (v/v) epinephrine, 0.24% (v/v) transferrin, 1% (v/v) penicillin/streptomycin and 0.1% (v/v) bovine pituitary extract. The cells were cultured in 95% air and 5% CO2 at 37° C. and maintained free of mycoplasma contamination.

Cell Viability Assay

BEAS-2B cells (~15,000 cells per well) in 200 μL of a complete medium, were seeded into a 96-well plate and allowed to attach for one day at 37° C. under humidified atmosphere of 5% CO2/95% air. Final concentrations of 40 μM, 20 μM, 10 μM, 5 μM, and 1 μM of CPs were added into the complete media by dilution with CPs stock solutions. After addition of CPs, cells were incubated for another 18 h. The cells were treated with 10 μL of methylthiazole tetrazolium (MTT) (5 mg/mL in PBS, CALBIOCHEM, Germany) and incubated for 4 h at 37° C. Subsequently, 200 μL of medium was removed by using a pipette and then 100 μL of biological grade DMSO (Sigma Aldrich, St. Louis, Mo., USA) was added to solubilize the purple formazan crystals formed by proliferating cells. Absorbance was measured by a microplate well reader (infinite M1000 PRO, TECAN, Switzerland) at 570 nm, Relative cell viability (%), FIG. 9, as a function of CPs concentration was expressed as the percentage relative to the untreated control cells. All measurements were performed in triplicate and standard deviation was included in the error bar.

Gel Retardation Assay

The siRNA binding capabilities of Poly-1 and Poly-2, respectively, were examined by a gel retardation assay as indicated in FIG. 10. 10 μL of siHDAC (400 nM) (Santa Cruz Biotechnology) was mixed with 10 μL of the polymers with different concentrations. Samples were gently vortexed and kept for 30 m at room temperature. Then, polyplexes solutions (20 μL) were mixed with 20 μL, of 2×RNA loading buffer (Thermo Fisher Scientific). The polyplexes solutions (40 μL) were loaded in to 40% poly (acrylamide) gel (cross-linking of 2.67) and run in 1× TBE buffer at 90V for 80 m. Free siHDAC bands were visualized using 0.5 μg/mL ethidium bromide solution. The bands were visualized by using the Quantity One software (Bio-Rad Laboratories, USA) and the density values are normalized to free siRNA.

Immunocytochemistry for Cilia to Determine Differentiation.

NHBE cells were allowed to re-differentiate for 21 days at the air-liquid interface on transwell filters. Re-differentiation was determined by staining for ciliation as described in Chinnapaiyan et al. *PLoS One* 2017. 12(1): p. e0169161. Cells were fixed in 4% paraformaldehyde in PBS, pH 7.4 for 15 min and permeabilized with 1% Triton X-100 in PBS for 20 min at room temperature (RT). After permeabilization, cells were washed with PBS and then blocked with 3% BSA in PBS for 1 h at room temperature. Cells were treated with the primary antibody [mouse anti human acetylated α-tubulin (Sigma Cat. #T6793; 1:1000)] in blocking solution and incubated overnight at 4° C. Cells were washed three times and then incubated with Alexa 647 anti mouse IgG for 45 min. Cells were washed three times with blocking solution and counterstained with 4,6-diamidine-2-phenylindole (DAPI, RPL) to label nuclei for 10 min. Transwell filters were excised and placed directly on the slide and images were acquired on visualized using a Zeiss fluorescence microscope with high resolution Axiocam 506 mono microscope camera (Zeiss, Germany). Cilia appear green at the apical side of the NHBE cultures with nuclei stained in blue.

Confocal Microscopic Images of BEAS-2B Cells.

BEAS-2B cells ($0.5 \times 10^6$/well) were seeded into a 12-well plate with glass coverslip one day prior to CP treatment, and then cultured in a complete media for 24 h under 5% $CO_2$ at 37° C. Cells were washed three times with 1× PBS after removing the media. The polyplex formed by mixing 10 μM CPs and siGLO (100 nM) was added to cells and then incubated for 48 h. After 48 h incubation, cells were washed three times with 1× PBS and fixed with 4% PFA for 10 m. Cells were then washed three times with 1× PBS and coverslips were mounted on microscope slides using a 1:1 glycerol/PBS mounting medium. Fluorescent images of the cells were obtained using an Olympus Fluorview FV1200 confocal microscope (Melville, N.Y. USA) equipped with a bandpass filter for green (513-556 nm) and a 60× oil immersion len (NA 1.35, n=1.519 immersion oil). Image J software (Version 1.50b, U.S. National Institute of Health, Bethesda, Md., USA) was used to process the image.

Confocal Fluorescence Microscopic Images of Primary NHBE Cells.

NHBE cells were treated with polyplex containing siGLO as described, above. After 48 h incubation, cells were washed three times with 1× PBS and fixed with 4% PFA for 10 m. Cells were then washed three times with 1× PBS. The cells grown on semipermeable membrane were separated from the chamber and then mounted on a microscope slide using a 1:1 glycerol/PBS mounting medium followed by sealing with nail polish. Fluorescent images of the cells were obtained using an Olympus Fluorview FV1200 confocal microscope (Melville, N.Y. USA) equipped with a bandpass filter (513-556 nm) and a 60× oil immersion lens (NA 1.35). Image J software (Version 1.50b, U.S. National Institute of Health, Bethesda, Md., USA) was used to process the image.

Gene Knockdown Experiment in BEAS-2B Cells

Lipofectamine RNAiMAX-Mediated Transfection of siHDAC in BEAS-2B Cells.

High-capacity cDNA reverse transcription kit was purchased from Applied Biosystems. Taqman Fast Advanced Master Mix was purchased from Life Technologies. Lipofectamine® RNAiMAX Transfection Reagent and Opti-MEM™ Reduced-Serum Medium were purchased from Thermo Fisher Scientific. BEAS-2B cells were plated on collagen coated tissue culture plates at a density of $0.6 \times 10^6$. Twenty-four hours following plating, cells were transfected with siHDAC complexed with Lipofectamine RNAiMax in Opti-MEM medium according to manufacturer's instructions using different concentrations of the siRNA (i.e., 12.5, 25, 50, 75, and 100 nM). BEAS-2B cells treated with equivalent amounts of lipofectamine RNAiMAX in Opti-MEM was used as transfection control, as shown in FIG. 13. The mixture was vortexed and incubated at room temperature for 30 m before adding to the cells. After eight-hour post-transfection, experiments were terminated, and total RNA was isolated and analyzed by quantitative RT-PCR.

Polymer-Mediated Transfection of siHDAC in BEAS-2B Cells.

The polyplex solutions were freshly prepared prior to transfection experiments. One day after plating BEAS-2B cells ($0.6 \times 10^6$) in a 12-wells plate, cells were transfected by adding polyplex solutions. 5 mM polymer stock solution was diluted to 5, 10, 20, and 40 μM, respectively, in 50 μl of RNase and DNase free water, and then mixed with various amounts of siHDAC (i.e., 12.5, 25, 50, 75, and 100 nM). Polyplex solution was vortexed for 30 m. Cells were incubated with polyplex for 48 h. The total RNA was analyzed by quantitative RT-PCR, as indicated in FIG. 13.

Gene Knockdown Experiment in NHBE Cells

The polyplex solutions were freshly prepared prior to transfection experiments. NHBE cultures re-differentiated at the air-liquid interface (ALI) were transfected by adding polyplex solutions using a protocol identical to that for BEAS2B cells above. Separately, another set of NHBE air-liquid interface cultures were treated with siRNA complexed with Lipofectamine RNAimax for comparison. Experiments proceeded for 48 hours and total RNA was isolated and analyzed by quantitative RT-PCR, as indicated in FIG. 13.

Total RNA was extracted from cells treated with transfection agents after 48 h incubation using an RNeasy mini kit (Qiagen Inc. Valencia, Calif.). The concentration and integrity of the extracted RNA were analyzed by measurement of the OD260/280 (Synergy™ HTX Multi-Mode Microplate Reader, Winooski, Vt., USA). Complementary DNA (cDNA) was reversely transcribed by using the Applied Biosystems High performance kit (Applied Biosystem, Carlsbad, Calif.). Reverse transcription of 2 µg of total cellular RNA was performed in a final volume of 20 µl containing 10 µl of RNA, 2 µl of 10× RT buffer, 0.8 µl of dNTP Mix (100 mM), 2.0 µl of 10× RT random hexamer primers, 1.0 µl of MultiScribe™ reverse transcriptase, 1 µl of RNase inhibitor, and 3.2 µl of nuclease-free water. The reverse transcription reaction was allowed to proceed using cycling parameters recommended by the manufacturer: an initial incubation at 25° C. for 10 m followed by incubation at 37° C. for 120 m. The reverse transcription was terminated by incubating at 85° C. for 5 sec. cDNA samples were stored at 20° C. until further use for quantitative PCR. Quantitative PCR was performed on the Bio-Rad CFX96 real-time system (BioRad, Hercules, Calif., USA) using validated TaqMan probes (GAPDH, HDAC2) according to manufacturer recommended cycling parameters (an initial denaturation cycle of 95° C. for 20 s followed by 40 cycles of 95° C./3 s and 60° C./30 s. qRT-PCR results are represented as relative quantification normalized to internal control (GAPDH).

Ussing Chamber Method to Determine Apical CFTR Activity

Ussing chamber electrophysiology was used to confirm re-differentiation and polarization as per: Unwalla et al. *Am. J. Respir. Cell. Mol. Biol.* 2015, 52 (1), 65-74; and Chinnapaiyan et al., *Sci Rep.* 2018, 8(1), 7984. CFTR is located at the apical side (mucosal) of the airway epithelium. Briefly, NHBE cultures were re-differentiated at the air-liquid interface. Following re-differentiation for 21 days, the snap wells were removed from supports and mounted in Ussing chambers. The short circuit current was measured and allowed to stabilize followed by addition of amiloride (10 µM) added apically to eliminate epithelial sodium channel (ENaC) influences. CFTR activation was affected by addition of albuterol (10 µM) and change in short circuit current ($\Delta I_{SCc}$) was determined. CFTR specificity was confirmed by addition of CFTR inhibitor $CFTR_{inh}172$ (20 µM) and the decrease in $\Delta I_{SC}$ was recorded.

All patents and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A modulated guanidine substituted polymer or nanoparticle, comprising a guanidine moiety on a plurality of repeating units of a polymer, or on the surface of a nanoparticle, the modulation being a substituted amidinourea or amidinocarbamate or salt thereof.

2. The modulated guanidine substituted polymer or nanoparticle according to claim 1, wherein the modulation is the substituted amidinourea or salt thereof.

3. The modulated guanidine substituted polymer or nanoparticle according to claim 2, wherein the substituted amidinourea or salt thereof has a hydrophobic modulation.

4. The modulated guanidine substituted polymer or nanoparticle according to claim 3, wherein the hydrophobic modulation is an N-alkylamino, N-arylamino, N-(alkylaryl) amino, N-(aryalkyl)amino, N,N-dialkylamino, N,N-diarylamino, N,N-di(alkylaryl)amino, N,N-di(aryalkylamino), N-alkyl,N-arylamino, N-alkyl,N-(alkylaryl)amino group, N-alkyl,N-(arylalkyl)aminoN-aryl,N-(alkylaryeamino group, or N-aryl,N-(arylalkyl)amino group.

5. The modulated guanidine substituted polymer or nanoparticle according to claim 4, wherein the alkyl group is a $C_2$ to $C_{22}$ straight, branched, cycloalkyl or alkyl substituted cycloalkyl group and/or the aryl group is a $C_6$ to $C_{22}$ mono- or polycyclic aromatic group.

6. The modulated guanidine substituted polymer or nanoparticle according to claim 3, wherein the hydrophobic modulation is a heterocyclic modulation.

7. The modulated guanidine substituted polymer or nanoparticle according to claim 6, wherein the heterocyclic modulation is an unsubstituted or substituted morpholine, pyrolidine, pyrrolc, piperidine, ethyleneimine, indole, isoindole, or carbazole.

8. The modulated guanidine substituted polymer or nanoparticle according to claim 2, wherein the substituted amidinourea or salt thereof has a hydrophilic modulation.

9. The modulated guanidine substituted polymer or nanoparticle according to claim 6, wherein the hydrophilic modulation is imidazole, purine, aminoethanol, or amino terminal polyethylene oxide.

10. The modulated guanidine substituted polymer or nanoparticle according to claim 1, wherein the modulation is a substituted or unsubstituted amidinocarbamate or salt thereof.

11. The modulated guanidine substituted polymer or nanoparticle according to claim 1, wherein the amidinocarbamate or salt thereof comprises a substituted or unsubstituted alky carbamate, aryl carbamate, alkylaryl carbamate or aryalkyl carbamante.

12. The modulated guanidine substituted polymer or nanoparticle according to claim 1, wherein the polymer is a conjugated polymer.

13. The modulated guanidine substituted polymer or nanoparticle according to claim 12, wherein the conjugated polymer comprises poly(phenyleneethynylene), poly(phenylenevinylene), poly(phenylene), poly(fluoreine), polythiophene, or any p-electron conjugated polymers.

14. The modulated guanidine substituted conjugated polymer or nanoparticle according to claim 1, wherein the nanoparticle comprises silica, alumina, titania, zinc oxide, tin oxide, silver oxide, cuprous oxide, cupric oxide, ceria, vanadium oxide zirconia, molybdenum, tungsten oxide, barium oxide, calcium oxide, iron oxide, and nickel oxide.

15. The modulated guanidine substituted polymer or nanoparticle according to claim 1, wherein the polymer is a natural or synthetic polymer.

16. A method of preparing a modulated guanidine substituted polymer or nanoparticle according to claim 1, comprising:

providing a N-Boc protected guanidine substituted polymer or N-Boc protected guanidine substituted nanoparticle and a solvent to form a solution or suspension;

adding an amine or an alcohol to the solution or suspension to make a reaction solution or suspension;

heating the solution or suspension to a temperature of at least 80° C.; and isolating the modulated guanidine substituted conjugated polymer or nanoparticle or a suspension or solution thereof.

17. A cancer treatment, comprising:

providing a modulated guanidine substituted polymer or nanoparticle according to claim 1;

combining the modulated guanidine substituted polymer or nanoparticle with a vehicle and, optionally, adjuvants to deliver the modulated guanidine substituted conjugated polymer or nanoparticle to form a therapeutic formulation;

delivering the therapeutic formulation to a cancer patient.

* * * * *